(12) United States Patent
Hollander

(10) Patent No.: US 7,151,162 B2
(45) Date of Patent: Dec. 19, 2006

(54) NUCLEAR PROTEIN

(75) Inventor: Georg Andreas Hollander, Basel (CH)

(73) Assignee: The University of Children's Hospital of Both Cantons of Basel, Basel (CH)

(*) Notice: Subject to any disclaimer, the term of this patent is extended or adjusted under 35 U.S.C. 154(b) by 0 days.

(21) Appl. No.: 10/309,175

(22) Filed: Dec. 4, 2002

(65) Prior Publication Data

US 2003/0148347 A1 Aug. 7, 2003

Related U.S. Application Data

(60) Provisional application No. 60/336,176, filed on Dec. 6, 2001.

(51) Int. Cl.
| | |
|---|---|
| *C07K 1/00* | (2006.01) |
| *C07K 14/47* | (2006.01) |
| *C07H 21/04* | (2006.01) |
| *C12P 21/02* | (2006.01) |
| *C12N 5/06* | (2006.01) |

(52) U.S. Cl. .................. 530/350; 435/5; 435/69.1; 435/69.7; 435/320.1; 435/325; 435/6; 536/23.2; 530/300; 530/388.1

(58) Field of Classification Search .................. 435/5, 435/69.1, 69.7, 325, 6, 320.1; 436/518; 536/23.2; 530/388.1, 350, 300
See application file for complete search history.

(56) References Cited

U.S. PATENT DOCUMENTS 6,239,161 B1  5/2001  Tang et al.

FOREIGN PATENT DOCUMENTS

| WO | WO 01/53455 | 7/2001 |
|---|---|---|
| WO | WO 01/54733 | 8/2001 |
| WO | WO 01/74851 | 10/2001 |

OTHER PUBLICATIONS

Acession No. S67766.*
Nature Genetics, 1999, 21:440-443).*
Journal of Cell Science 2001; 114, 2043-2053.*
Alberts et al. (Molecular Biology of the Cell, 3rd edition, 1994, p. 465).*
Campbell, monoclonal antibody technology 1984, Chapter 1, p. 29.*
EMBL database Accession No. BB599521, XP-002240709 (2003).
EMBL database Accession No. AC021028, XP-002240710 (2002).
Brennan et al. "Wnt proteins in mammary development and cancer" J. Mammary Gland Biol. Neopl. 9:119-131 (2004).
Doucas et al. "Changes in the wnt signalling pathway in gastrointestinal cancers and their prognostic significance" Eur. J. Cancer 41:365-279 (2005).
Li et al. "CTNNB1 mutations and overexpression of wnt/β-catenin target genes in WT1-mutant Wilms' tumors" Am. J. Pathol. 165:1943-1953 (2004).
Mazieres et al. "Wnt signaling in lung cancer" Cancer Lett. 222:1-10 (2005).
Waterman "Lymphoid enhancer factor/T cell factor expression in colorectal cancer" Cancer Metastasis Rev. 23:41-52 (2004).
Int'l Preliminary Examination Report dated Apr. 4, 2004.
Int'l Search Report dated May 12, 2003.
Choi et al. "Lad, an adapter protein interacting with the SH2 domain of $p56^{ICR}$, is required for T cell activation" J. Immunol. 163:5242-5249 (1999).
Peifer et al. "Wnt signaling on oncogenesis and embryogenesis—a look outside the nucleus" Science 287:1606-1609 (2000).
Polakis "Wnt signaling and cancer" Genes & Development 14:1837-1851 (2000).
Sawyer "Src homology-2 domains: Structure, mechanisms, and drug discovery" Biopolymers 47:243-261 (1998).
Spurkland et al. "Molecular cloning of a T cell-specific adapter protein (TSAd) containing an Src homology (SH) 2 domain and putative SH3 and phosphotyrosine binding sites" J. Biol. Chem. 273:4539-4546 (1998).

* cited by examiner

*Primary Examiner*—Nita Minnifield
*Assistant Examiner*—Padma Baskar
(74) *Attorney, Agent, or Firm*—Nixon & Vanderhye P.C.

(57) ABSTRACT

An isolated Shoca polypeptide comprising:
(i) the amino acid sequence of SEQ ID NO: 2 or SEQ ID NO: 4; or
(ii) a variant thereof which is capable of interacting with a polypeptide of the wnt signalling pathway; or
(iii) a fragment of (i) or (ii) which is capable of interacting with a polypeptide of the wnt signalling pathway, a polypeptide encoding said polypeptide, a method for identifying a modulator of the wnt signalling pathway utilising said polypeptide or polynucleotide and methods of diagnosing and treating cancer.

2 Claims, 7 Drawing Sheets

Fig. 2

```
hShoca-1        1 MLQQILHDMYIDPELLAELSDVQKHILFYKMREEQLRRWKERETWEALAQDEGLRPPKTK    60
mShoca-1        1 MLQQILQDMYIDPELLAELSDVQKHILFYKMREEQLRRWKEREAWDALAQAEGLRPAKVK    60
hShoca-2        1 MLKQILSEMYIDPDLLAELSEEQKQILFFKMREEQIRRWKEREAAMERKESLPVKPRPKK    60
mShoca-2        1 MLRQILSDMFIDPDLLAELSEEQKQILFYKMREEQIRRWKEREAAMERKESLPVKSRPKK    60
EST Zebra fish A 1 MLQQILKDMYIDPDVLEALNDEQKKMLFLKMREEHVRRWKEREEKLEREPLKP---KAKT    57
EST Zebra fish B 1 MLQQILADMYIDPDVLEALNEEQKKILFFKMREEQVRRWKEREEQESKGEIKKEKLRKKK    60
                  *.:**.:.*: *.: ::::***** ::** :* hShoca-1       61 RAASDKHIQWLLGADGEVWVWIMGEGPGDKPYEEISEELIAERARLQAQREAEELWRQKE   120
mShoca-1       61 RAS-NKHLQWLLGADGEVWVWVMGEGPGDKPYEEISEELIAERARLQAQKEAEELWRQKE   119
hShoca-2       61 ENG--KSVHWKLGADKEVWVWVMGEHHLDKPYDVLCNEIIAERARLKAEQEAEEPRKTHS   118
mShoca-2       61 ENG--KSVHWKLGADKQVWVWVMGEHHLDKPYDVLCDEILAEREHLRAAKDSE-LRKTQS   117
EST Zebra fish A 58 AHS--KSVSWLLGRDGDVQVIVIGEMDEFKSSKIIYSG---------------------    93
EST Zebra fish B 61 GPC--KNVSWLLGRDGDVHVCIIGESDVLESPKLILSELRNNTTANGNNINRANAESIKS   118
                       * *.  **  ..*   :  **   :.**   : ::.

hShoca-1      121 AEITKKFRDALANEKARILAEKWKVEMEDRKAAKVLEERIHEEFKRKEEEERKRGEEEQIR   180
mShoca-1      120 AEITKKFRDALANEKARILAEKWKVEMEDRKAAKILEERIHEEFKRKEEEERRKRGEEQIR   179
hShoca-2      119 EEFTNSLKTKSQYHDLQAPDNQQTKDIWKKVAEKEELEQGSRPAPTLEEKIRSLSSSSR-   178
mShoca-2      118 LELANSLKIKSQNCDLQAMKKTEPQNVTRKAASEEASGQGPRAIPTRKDDKAQTKP----   173
EST Zebra fish A                                                                   --
EST Zebra fish B 119 SSIKLNRVQXTSTEPGIQLLI---------------------------------------   139
```

Fig. 3

```
hShoca-1  327 WFHGIISREDAEALLENMTEG-AFLVRVSEKIWGYTLSYRLQKGFKHFLVDASGDFYSFL 385
mShoca-1  325 WFHGIISRESAEDLLENMTEG-AFLVRVSEKIWGYTLSYRLQRGFKHFLVDASGDFYSFL 383
hShoca-2  347 WFHGILTLKKANELLLSTGMPGSFLIRVSERIKGYALSYLSEDGCKHFLIDASADAYSFL 406
mShoca-2  315 WFHGILTLKKANELLS-TGVPGSFLIRVSEKIKGYALSYLSEEGCKHFLIDASANSYSFL 373
              ****:: .:.*: ********:*:***:**:*******::* ****:***::* ****.:

hShoca-1  386 GVDPNRHATLTDLVDFHKEEIITVSGGELLQEPCGQRDSPPDYHLLFE 433
mShoca-1  384 GVDPNRHATLTDLIDFHKEEIITVSGGELLQEPCGQRDSPPDYHLLFE 431
hShoca-2  407 GVDQLQHATLADLVEYHKEEPITSLGKELLLYPCGQQDQLPDYLELFE 454
mShoca-2  374 GVDQLQHATLADLVEYHKEEPITSLGKELLYPCGQQDKLPDYLELFQ 421
              ***  ****:**::.:*** :*. *:***  ****:*  ***  **.:
```

Fig. 4

```
hShoca-1    MLQQILHDMYIDPELLAELSDVQKHILFYKMREEQLRRWKERETWEALAQDEGLRPFKTK 60
mShoca-1    MLQQILQDMYIDPELLAELSDVQKHILFYKMREEQLRRWKEREAWDALAQAEGLRPAKVK 60
            ******:*********************************:*:.*:******.***.*:

hShoca-1    RAASDKHIQWLLGADGEVWVWIMGEGPGDKPYEEISEELIAERARLQAQREAEELWRQKE 120
mShoca-1    RAS-NKHLQWLLGADGEVWVWMGEGPGDKPYEEISEELIAERARLQAQKEAEELWRQKE 119
            : .::**********:*********************:******* hShoca-1    AEITKKFRDALANEKARILAEKWKVEMEDRKAAKVLEERIHEEFKRKEEEERKRGEEQIR 180
mShoca-1    AEITKKFRDALANEKARILAEKWKVEMEDRKAAKILEERIHEEFKRKEEEERRRGEEQIR 179
            ********************************:*************:*** hShoca-1    LQEEQRAKELYWTLKQAQLHCQASEKEEREWEEQLRRSKAADEERSRRAQRARDEYRHHS 240
mShoca-1    LQEEQRAKEIYWTLKQAQLHSQASENEEREWEEQLRRSKAADEERSRRAQRARDEYRRHS 239
            *********:**********.****:******************************:**

hShoca-1    LRAIQKGTVAGLSSMFRELGQSHEQEARLYHHLPDPGLPQPLALPVSRTWERPLRPVSRD 300
mShoca-1    LRAIQKGTVAGLSTMFQELGQNHEQEARLYHQLPDTSPPSPLTGPD-RTWERPLRPLSRE 298
            *************:**:****.*********:***..*  **. ** ********:**:

hShoca-1    VIVRWFKEEQLPRRAGFERNTKFIAPWFHGIISREDAEALLENMTEGAFLVRVSEKIWGY 360
mShoca-1    VIVRWFKEEQLPRRAGFERNTKSIAPWFHGIISRESAEDLLENMTEGAFLVRVSEKIWGY 358
            ********************.*******.:******************** hShoca-1    TLSYRLQKGFKHELVDASGDEYSFLGVDPNRHATLTDLVDFHKEEIITVSGGELLQEPCG 420
mShoca-1    TLSYRLQRGFKHFLVDASGDEYSFLGVDPNRHATLTDLIDFHKEEIITVSGGELLQEPCG 418
            *****:.*********************:***************** hShoca-1    QRDSPPDYHLLFE 433
mShoca-1    QRDSPPDYHLLFE 431
            *************
```

US 7,151,162 B2

NUCLEAR PROTEIN

This application claims the benefit of provisional Appln. No. 60/336,176, filed Dec. 6, 2001; the entire content of which is hereby incorporated by reference in this application.

FIELD OF THE INVENTION

The present invention relates to a novel signalling protein associated with healthy, neoplastic and oncogenic tissues. The invention also relates to screening methods for identifying modulators of activity and/or expression of the signalling protein and to associated methods of diagnosis, prognosis and therapy of cancer.

BACKGROUND TO THE INVENTION

Human cancer results from the accumulation of independent genetic alterations which effect the transcriptional programs normally responsible for controlling cell growth and survival. Cancers within a single clinical category may exhibit seemingly disparate genetic defects that are, however, part of a common signal transduction pathway. The discovery of the wnt signalling pathway (summarised in FIG. 1) and the structure/function analysis of its distinct molecular components has provided an outstanding example for the identification of common denominators in oncogenesis (Polakis (2000) *Genes & Development* 14:1837–1851; Peifer and Polakis (2000) *Science* 287: 1606–1609).

Wnt signalling is initiated by members of the family of secreted wnt glycoproteins which bind to one or several of their specific cell surface receptors, designated frizzled. This family of seven-path-transmembrane receptors activate the dishevelled protein upon binding of their respective ligand. Associated with axin, dishevelled prevents glycogen synthase kinase-3β from phosphorylating critical substrates such as β-catenin. Other substrates include the negative regulators axin itself and APC. Unphosphorylated β-catenin escapes degradation via the ubiquitin pathway and translocates to the nucleus where it associates with transcription factors such as T-cell factor (TCF) and leucocyte enhancer factor (LEF). In mammals, the number of identified target genes transcriptionally regulated by way of wnt signalling is still limited but includes c-myc, cyclin D1, c-jun, matrix metalloproteinases and CD44.

There have been numerous reports on transcipional overexpression, and sometimes underexpression, of wnt genes in human cancers but mRNA expression levels are merely correlative. More compelling evidence for the involvement of wnt-mediated signals in neoplastic transformation stems from mutational analysis of regulatory genes operational in wnt signal transduction. For example, certain mutations in β-catenin render this protein refractory to inhibition by APC and thus prevent its degradation. In consequence, constitutive activation of β-catenin/TCF regulated gene transcription occurs. Similarly, mutational changes in APC and axin can disrupt the normal regulation of β-catenin and have been associated with various forms of tumours. Thus, characterizing wnt molecules, their signal transduction pathway and their biological effects will further aid the interpretation of direct and epigenetic evidence implicating wnts in oncogenesis including the generation of colorectal carcinoma, familial adenomatous polyposis, sporadic desmoid (i.e. aggressive fibromatosis), gastric cancer, hepatoblastoma, Wilm's tumor, melanoma, pancreatic tumors, anaplastic thyroid tumors, medulloblastoma, endometrial ovarian cancer, prostate cancer, and acute lymphoblastic leukemia.

BRIEF DESCRIPTION OF THE FIGURES

FIG. 2 is a comparison of the N-terminal amino acid sequences of mouse, human and zebra fish Shoca proteins.

FIG. 3 is a comparison of the SH2 domain of mouse and human Shoca-1 and Shoca-2.

FIG. 4 is an alignment of the amino acid sequences of mouse and human Shoca-1.

BRIEF DESCRIPTION OF THE SEQUENCES

Figure 1:
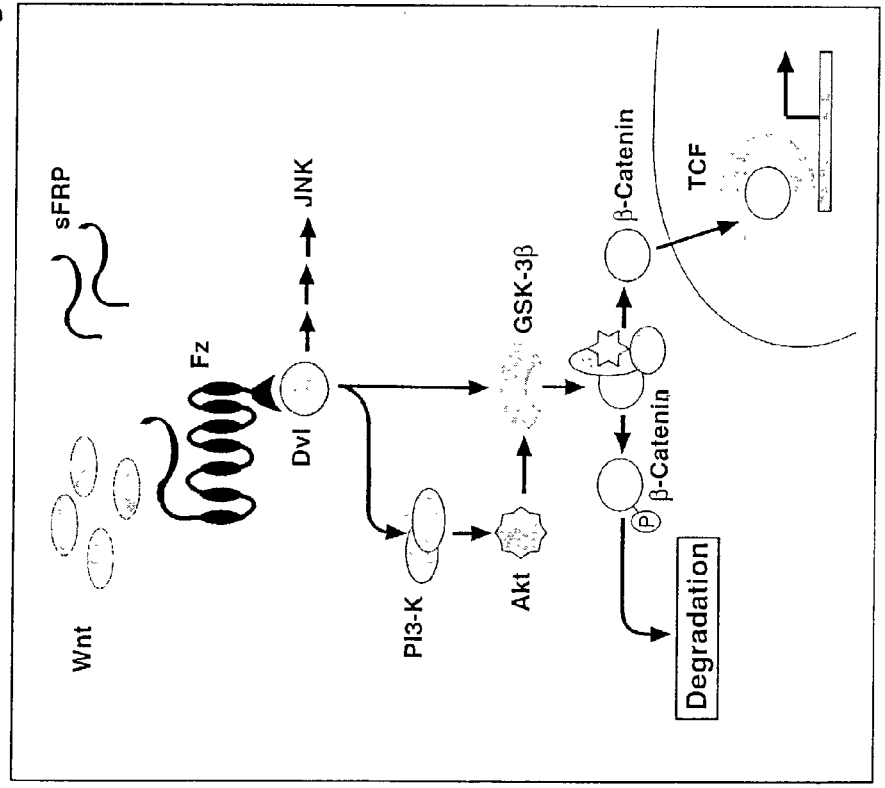
FIG. 1 is a schematic picture of the Wnt signaling pathway. The abreviations used are:
sFRP: sluable Frizzled Receptor Protein
Fz: Frizzled
Dvl: Dishevelled
JNK: Jun-kinase pathway
PI3-K: Phosphatidylinositide 3 OH Kinase
Akt: Protein Kinase B
GSK-3β: Glycogen Synthase Kinase 3β
TCF: T Cell Factor
Figure 5:
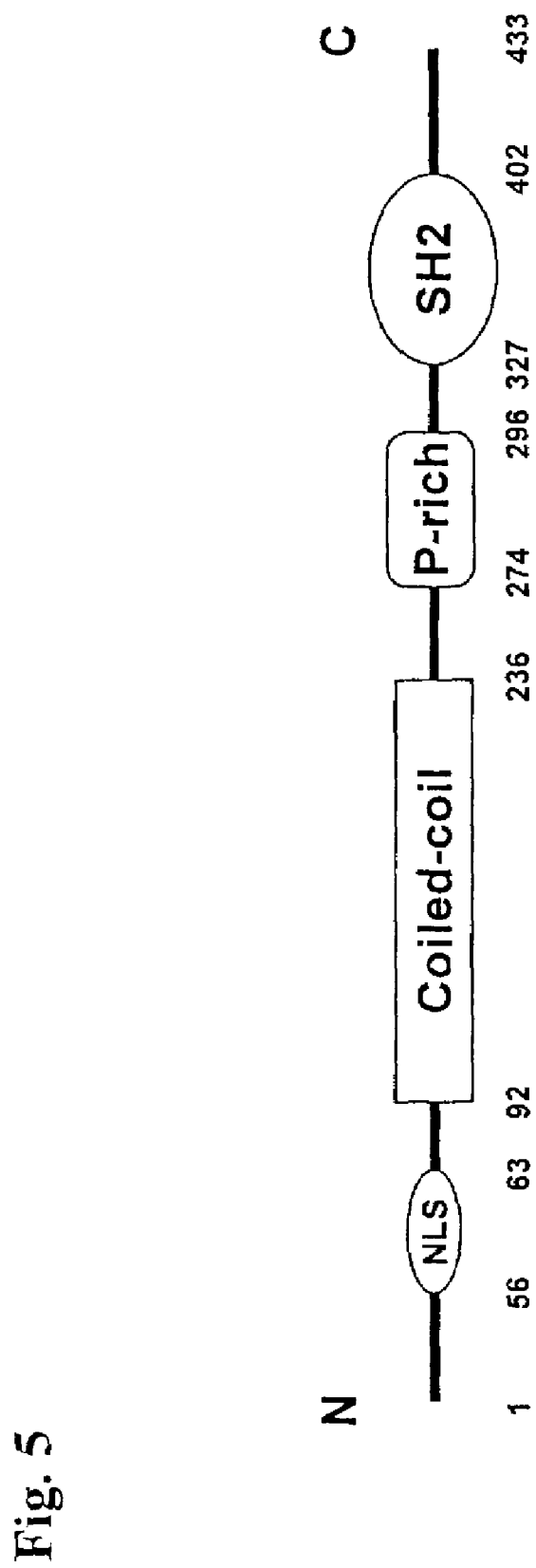
FIG. 5 shows a structure prediction of Shoca-1, revealing a coiled-coiled domain and a C-terminally located SH2 domain.

SEQ ID NO: 1 shows the nucleotide and amino acid sequences of murine Shoca-1.
SEQ ID NO: 2 shows the amino acid sequence of murine Shoca-1.
SEQ ID NO: 3 shows the nucleotide and amino acid sequences of human Shoca-1.
SEQ ID NO: 4 shows the amino acid sequence of human Shoca-1.
SEQ ID NO: 5 shows the nucleotide and amino acid sequences of murine Shoca-2.
SEQ ID NO: 6 shows the amino acid sequence of murine Shoca-2.
SEQ ID NO: 7 shows the nucleotide and amino acid sequences of human Shoca-2.
SEQ ID NO: 8 shows the amino acid sequence of human Shoca-2.
SEQ ID NO: 9 shows the N-terminal amino acid sequence of human Shoca-1.
SEQ ID NO: 10 shows the N-terminal amino acid sequence of murine Shoca-1.
SEQ ID NO: 11 shows the N-terminal amino acid sequence of human Shoca-2.
SEQ ID NO: 12 shows the N-terminal amino acid sequence of murine Shoca-2.
SEQ ID NO: 13 shows the N-terminal amino acid sequence of zebra fish homologue A.
SEQ ID NO: 14 shows the N-terminal amino acid sequence of zebra fish homologue B.
SEQ ID NO: 15 shows the amino acid sequence of the SH2 domain of human Shoca-1.

SEQ ID NO: 16 shows the amino acid sequence of the SH2 domain of murine Shoca-1.

SEQ ID NO: 17 shows the amino acid sequence of the SH2 domain of human Shoca-2.

SEQ ID NO: 18 shows the amino acid sequence of the SH2 domain of murine Shoca-2.

SEQ ID NO: 19 shows the amino acid sequence of peptide Shoca #0 used to generate Shoca antibodies.

SEQ ID NO: 20 shows the amino acid sequence of peptide Shoca #1 used to generate anti-Shoca antibodies.

SEQ ID NO: 21 shows the amino acid sequence of peptide Shoca #2 used to generate anti-Shoca antibodies.

SEQ ID NO: 22 shows the amino acid sequence of peptide Shoca #3 used to generate anti-Shoca antibodies.

SEQ ID NO: 23 shows the amino acid sequence of peptide Shoca #4 used to generate anti-Shoca antibodies.

SEQ ID NO: 24 shows the amino acid sequence of peptide Shoca #5 used to generate anti-Shoca antibodies.

SUMMARY OF THE INVENTION

The present inventors have identified in mouse and human tissue a novel gene whose product is directly involved in wnt-mediated signalling. The gene (SEQ ID NO: 1 and SEQ ID NO: 3) encodes an SH2-domain containing adaptor protein of 52 kDa (as demonstrated by Western blotting) and has thus been designated Shoca-1. Subsequently, a second mouse Shoca-like gene (Shoca-2) has been identified by use of EST analysis in the public domain (SEQ ID NO: 5). A human Shoca-2 homologue has also been identified on the basis of sequence homology (SEQ ID NO: 7).

The inventors have carried out an extensive molecular analysis of Shoca, characterised its function ex vivo and have shown that its expression in normal tissues is absent or low and that its expression is correlated with oncogenic changes in various tissues. The expression pattern of Shoca-1 and the functional effects of Shoca-mediated modulation of Wnt signals suggest a central role for this family of molecules in the process of cell fate determination. In analogy to other molecules affecting Wnt signal transduction, impairment of regular Shoca function may affect the cellular homeostasis in different tissues leading from physiological cell growth and differentiation to aberrant cell survival and function. In this context, detection of a functional aberration of Shoca has a diagnostic significance in the prediction of disease progression, therapeutic response and prognosis. Moreover, novel interacting molecules that modulate Shoca function will provide unique tools to interfere with uncontrolled cell differentiation and proliferation. The inventors have thus shown that Shoca may be important in regulating normal physiology and homeostasis of cells and that Shoca may be useful for diagnosis, risk assessment and therapy of human malignancies.

Accordingly, the present invention provides:

an isolated Shoca polypeptide comprising:
   (i) the amino acid sequence of SEQ ID NO: 2 or SEQ ID NO: 4; or
   (ii) a variant thereof which is capable of interacting with a polypeptide of the wnt signalling pathway; or
   (iii) a fragment of (i) or (ii) which is capable of interacting with a polypeptide of the wnt signalling pathway;

a polynucleotide encoding a polypeptide according to the invention;

a polynucleotide encoding a Shoca polypeptide capable of interacting with a polypeptide of the wnt signalling pathway, which polynucleotide comprises:

(i) the nucleic acid sequence of SEQ ID NO: 1 or SEQ ID NO: 3 and/or a sequence complementary thereto;
   (ii) a sequence which hybridizes under stringent conditions to a sequence defined in (i);
   (iii) a sequence that is degenerate as a result of the genetic code to a sequence as defined in (i) or (ii); or
   (iv) a sequence having at least 85% identity to a sequence as defined in (i), (ii) or (iii);

an expression vector comprising a polynucleotide according to the invention;

a host cell comprising a vector according to the invention;

an antibody specific for a polypeptide according to the invention;

a method of identifying an agent capable of modulating the wnt signalling pathway, which method comprises:
   (i) providing a polypeptide comprising the amino acid sequence of SEQ ID NO: 2 or 4, or a variant thereof, or a fragment of either thereof which variant or fragment is capable of interacting with a polypeptide of the wnt signalling pathway or a polynucleotide encoding said polypeptide; and a test agent;
   (ii) contacting the polypeptide or polynucleotide and the test agent; and
   (iii) determining whether the test agent has any effect on the expression of said polypeptide or on a function or property of said polypeptide thereby determining whether the test agent is capable of modulating Shoca activity;

an agent capable of modulating Shoca activity identified by a method according to the invention for use in a method of treatment of the human or animal body by therapy or in a method of diagnosis carried out on the human or animal body;

use of an agent identified by a method according to the invention in the manufacture of a diagnostic agent or a medicament for use in the diagnosis or treatment of cancer;

a method of diagnosing cancer which method comprises determining the level of Shoca expression in a tissue sample from a subject;

a method of predicting the progression of a tumour which method comprises determining the level of Shoca expression in a tissue sample from a subject;

use of an anticancer agent in the manufacture of a medicament for treating cancer in an individual wherein the individual has been diagnosed as having cancer using a method according to the invention; and a method of treating cancer, which method comprises:
   (i) identifying an agent capable of modulating Shoca activity; and
   (ii) administering a therapeutically effective amount of said agent to a human or animal subject in need to thereof.

DETAILED DESCRIPTION OF THE INVENTION

Proteins

The present invention relates to a novel protein of the wnt signaling pathway, referred to herein as Shoca, functional variants thereof and functional fragments of Shoca or of variants of Shoca. Sequence information for murine Shoca-1 is provided in SEQ ID NO: 1 (nucleotide and amino acid) and in SEQ ID NO: 2, sequence information for human Shoca-1 is provided in SEQ ID NO: 3 (nucleotide and amino acid) and in SEQ ID NO: 4, sequence information for murine Shoca-2 is provided in SEQ ID NO: 5 (nucleotide and amino acid) and in SEQ ID NO: 6 and sequence information for human Shoca-2 is provided in SEQ ID NO: 7 (nucleotide and amino acid) and in SEQ ID NO: 8. A polypeptide of the invention thus consists essentially of the amino acid sequence of SEQ ID NO: 2, 4, 6 or 8 or of a variant of any one of these sequences, or of a fragment of any one of these sequences or variants.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention. Routine methods can be employed to purify and/or synthesise the proteins according to the invention. Such methods are well understood by persons skilled in the art, and include techniques such as those disclosed in Sambrook et al, Molecular Cloning: a Laboratory Manual, $2^{nd}$ Edition, CSH Laboratory Press, 1989, the disclosure of which is included herein in its entirety by way of reference.

The term "variant" refers to a polypeptide which shares at least one property or function with Shoca-1. A "fragment" of the invention also possesses at least one function or property of Shoca-1. Shoca-1 is a signalling protein of the wnt signaling pathway. Shoca-1 may also be a signalling protein of any other pathway regulating cell survival, proliferation or differentiation. Preferably a variant polypeptide is one which is capable of interacting with a molecule of the wnt signalling pathway, preferably a nuclear molecule. Preferably, a variant polypeptide is capable of interacting with LEF, TCF and/or β-catenin. A variant may interact with an endogenous Shoca protein. Preferably the variant polypeptide is capable of modulating β-catenin-LEF/TCF regulated transcription. Preferably modulation of β-catenin-LEF/TCF transcription by a polypeptide of the invention is tissue specific, for example with repression occurring in thymic epithelial cells and stimulation occurring in fibroblasts.

A variant polypeptide of the invention may typically be identified by monitoring for a function of Shoca such as binding to LEF and/or TCF and/or β-catenin, modulating expression of a reporter gene under the control of LEF/TCF responsive control sequences.

The SH2 domain of Shoca-1 is essential for the repression of LEF/TCF mediated transcription in thymic epithelial cells. It is, therefore, preferred that a variant or fragment of Shoca comprises a functional SH2 domain. Other preferred fragments and variants and variants may comprise other functional domains of Shoca-1, such as a coiled-coil domain or a phosphorylation site.

Shoca is almost exclusively expressed in the nucleus. Preferred fragments and variants may contain a nuclear localisation sequence. Mutants of Shoca-1 missing the first N-terminal 50 amino acids fail to translocate from the cytoplasm to the nucleus, suggesting that a motif within this sequence contains a nuclear localisation sequence. It is, therefore, preferred that a variant or fragment of the invention comprises an N-terminal domain including a nuclear localisation sequence. More preferably, the variant or fragment contains the sequence from position 56 to position 63 of SEQ ID NO: 4.

In another aspect of the invention, a variant is one which does not show the same activity as Shoca but is one which inhibits a basic function of Shoca, i.e. has dominant-negative activity. For example, a variant polypeptide is one which inhibits modulation of LEF/TCF mediated transcription by Shoca.

The identity between the different Shoca proteins at the amino acid level are as follows: Human Shoca-1 is 91% identical to mouse Shoca-1; human Shoca-2 is 72% identical to mouse Shoca-2; human Shoca-1 is 40% identical to human Shoca-2; mouse Shoca-1 is 40% identical to mouse Shoca-2.

Typically, polypeptides with more than about 40% identity preferably at least 70%, at least 80% or at least 90% and particularly preferably at least 91% at least 95% at least 97% or at least 99% identity, with the amino acid sequence of SEQ ID NO: 2 or 4, are considered as variants of the proteins. Such variants may include allelic variants and the deletion, modification or addition of single amino acids or groups of amino acids within the protein sequence, as long as the peptide retains at least one function or property of Shoca. Preferably a variant of SEQ I NO: 2 or 4 will have the same domain structure as Shoca-1, i.e. a coiled-coil domain and/or a C-terminal SH2 domain.

Amino acid substitutions may be made, for example from 1, 2 or 3 to 10, 20 or 30 substitutions. The modified polypeptide generally retains activity as a wnt signaling molecule. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling (molecular breeding) techniques.

Shorter polypeptide sequences are within the scope of the invention. For example, a peptide fragment of at least 20 amino acids or up to 50, 60, 70, 80, 100, 150 or 200 amino acids in length is considered to fall within the scope of the invention as long as it demonstrates a basic biological functionality of Shoca. In particular, but not exclusively, this aspect of the invention encompasses the situation when the protein is a fragment of the complete protein sequence and may represent a LEF/TCF-binding region. Such fragments can be used to construct chimeric molecules. Such fragments of Shoca or a variant thereof can also be used to raise anti-Shoca antibodies.

WO 01/54733 identifies (amongst many others) an amino acid sequence of 235 amino acids in length corresponding to residue 220 through to 454 of the amino acid sequence of SEQ ID NO: 7. No function is attributed to this peptide in WO 01/54733. This peptide is not a preferred fragment in accordance with the present invention. WO 01/53455 identifies, amongst many others, SEQ ID NO: 931, the sequence of which, beginning at the fourth residue, corresponds to residues 266 through to 454 of the amino acid sequence of SEQ ID NO: 7. No specific function is attributed to this peptide in WO 01/53455. This peptide is not a preferred fragment in accordance with the present invention.

Polypeptides of the invention may be chemically modified, e.g. post-translationally modified. For example, they may be glycosylated or comprise modified amino acid residues. They may also be modified by the addition of histidine residues to assist their purification or by the addition of a nuclear localisation sequence to promote translocation to the nucleus. Such modified polypeptides fall within the scope of the term "polypeptide" of the invention.

Polynucleotides

The invention also includes nucleotide sequences that encode for Shoca or a variant or fragment thereof as well as nucleotide sequences which are complementary thereto. The nucleotide sequence may be RNA or DNA including genomic DNA, synthetic DNA or cDNA. Preferably the nucleotide sequence is a DNA sequence and most preferably, a cDNA sequence. Nucleotide sequence information for murine and human Shoca-1 is provided in SEQ ID NOs: 1 and 3 respectively and nucleotide sequence information for murine and human Shoca-2 is provided in SEQ ID NOs: 5 and 7 respectively. Such nucleotides can be isolated from cells or synthesised according to methods well known in the art, as described by way of example in Sambrook et al, 1989.

Typically a polynucleotide of the invention comprises a contiguous sequence of nucleotides which is capable of hybridizing under selective conditions to the coding sequence or the complement of the coding sequence of SEQ ID NO: 1. Such sequences include the sequences shown in SEQ ID NOs: 3, 5 and 7.

A polynucleotide of the invention can hybridize to the coding sequence or the complement of the coding sequence of SEQ ID NO: 1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 100 fold, as intense as interactions between other polynucleotides and the coding sequence of SEQ ID NO: 1. The intensity of interaction may be measured, for example, by radiolabelling the probe, e.g. with $^{32}P$. Selective hybridisation may typically be achieved using conditions of medium to high stringency. However, such hybridisation may be carried out under any suitable conditions known in the art (see Sambrook et al, 1989. For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 1, 3, 5 or 7 may be modified by nucleotide substitutions, for example from 1, 2 or 3 to 10, 25, 50 or 100 substitutions. The polynucleotide of SEQ ID NO: 1, 3, 5 or 7 may alternatively or additionally be modified by one or more insertions and/or deletions and/or by an extension at either or both ends. A polynucleotide may include one or more introns, for example may comprise genomic DNA. The modified polynucleotide generally encodes a polypeptide which has Shoca activity. Alternatively, a polynucleotide encodes a ligand-binding portion of a polypeptide or a polypeptide which modulates Shoca activity. Degenerate substitutions may be made and/or substitutions may be made which would result in a conservative amino acid substitution when the modified sequence is translated, for example as shown in the Table above.

The identity between the different Shoca proteins at the DNA level are as follows: Human Shoca-1 is 80% identical to mouse Shoca-1; human Shoca-2 is 75% identical to mouse Shoca-2, human Shoca-1 is 57% identical to human Shoca-2; and mouse Shoca-1 is 59% identical to mouse Shoca-2.

A nucleotide sequence which is capable of selectively hybridizing to the complement of the DNA coding sequence of SEQ ID NO: 1 or 3 will generally have at least 50%, at least 57%, at least 60%, at least 70%, at least 80%, at least 88%, at least 90%, at least 95%, at least 98% or at least 99% sequence identity to the coding sequence of SEQ ID NO: 1 over a region of at least 20, preferably at least 30, for instance at least 40, at least 60, more preferably at least 100 contiguous nucleotides or most preferably over the full length of SEQ ID NO: 1. Preferably the nucleotide sequence encodes a polypeptide which has the same domain structure as Shoca-1, i.e. a coiled-coil domain and/or a C-terminal SH2 domain.

For example the UWGCG Package provides the BESTFIT program which can be used to calculate homology (for example used on its default settings) (Devereux et al (1984) *Nucleic Acids Research* 12, p 387–395). The PILEUP and BLAST algorithms can be used to calculate homology or line up sequences (typically on their default settings), for example as described in Altschul (1993) J. Mol. Evol. 36:290–300; Altschul et al (1990) J. Mol. Biol. 215:403–10.

Software for performing BLAST analyses is publicly available through the National Centre for Biotechnology Information (ncbi.nlm. nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787 and Altschul and Gish (1996) *Methods Enzymol.* 266: 460–480. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

The nucleotides according to the invention have utility in production of the proteins according to the invention, which may take place in vitro, in vivo or ex vivo. The nucleotides may be involved in recombinant protein synthesis or indeed as therapeutic agents in their own right, utilised in gene therapy techniques. Nucleotides complementary to those encoding Shoca, or antisense sequences, may also be used in gene therapy.

The present invention also includes expression vectors that comprise nucleotide sequences encoding the proteins of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. 1989.

Flanking sequences upstream from the ATG site in the Shoca gene are important for the regulation of Shoca expression. It is preferred that flanking sequences needed for the proper expression of Shoca are included in expression vectors of the invention.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used as test compounds in the assays of the invention or may be useful in a method of treatment of the human or animal body by therapy.

Preferably, a polynucleotide of the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example in a method of gene therapy.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters include the metallothionein promoter which can be induced in response to heavy metals such as cadmium. Viral promoters such as the SV40 large T antigen promoter or adenovirus promoters may also be used. An IRES promoter may also be used. All these promoters are readily available in the art.

Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

The invention also includes cells that have been modified to express a Shoca polypeptide of the invention. Such cells include transient, or preferably stable higher eukaryotic cell lines, such as mammalian cells or insect cells, using for example a baculovirus expression system, lower eukaryotic cells, such as yeast or prokaryotic cells such as bacterial cells. Particular examples of cells which may be modified by insertion of vectors encoding for a polypeptide according to the invention include mammalian thymic epithelial cells, fibroblasts, HEK293T, CHO, HeLa, BHK, 3T3 and COS cells. A polypeptide of the invention may be expressed in cells of a transgenic non-human animal, preferably a mouse. A transgenic non-human animal expressing a polypeptide of the invention is included within the scope of the invention.

Antibodies

According to another aspect, the present invention also relates to antibodies, specific for a polypeptide of the invention. Such antibodies are for example useful in purification, isolation or screening methods involving immunoprecipitation techniques or, indeed, as therapeutic agents in their own right. Antibodies may be raised against specific epitopes of the polypeptides according to the invention.

Preferred antibodies are raised against the amino acid sequences shown in SEQ ID Nos: 19, 20 and 21.

Antibodies may be used to impair Shoca function. An antibody, or other compound, "specifically binds" to a protein when it binds with preferential or high affinity to the protein for which it is specific but does substantially bind not bind or binds with only low affinity to other proteins. A variety of protocols for competitive binding or immunoradiometric assays to determine the specific binding capability of an antibody are well known in the art (see for example Maddox et al, J. Exp. Med. 158, 1211–1226, 1993). Such immunoassays typically involve the formation of complexes between the specific protein and its antibody and the measurement of complex formation.

Antibodies of the invention may be antibodies to human polypeptides or fragments thereof. For the purposes of this invention, the term "antibody", unless specified to the contrary, includes fragments which bind a polypeptide of the invention. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies may be used in a method for detecting polypeptides of the invention in a biological sample, which method comprises:

I providing an antibody of the invention;
II incubating a biological sample with said antibody under conditions which allow for the formation of an antibody-antigen complex; and
III determining whether antibody-antigen complex comprising said antibody is formed.

A sample may be for example a tissue extract, blood, serum and saliva. Antibodies of the invention may be bound to a solid support and/or packaged into kits in a suitable container along with suitable reagents, controls, instructions, etc. Antibodies may be linked to a revealing label and thus may be suitable for use in methods of in vivo Shoca imaging.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495–497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus and in transgenic mice enabling production of human antibodies.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Assays

An important aspect of the present invention is the use of polypeptides according to the invention in screening methods. The screening methods may be used to identify substances that bind to Shoca polypeptides or mRNAs. Screening methods may also be used to identify modulators, which may be inhibitors or activators of Shoca activity, and/or agents which up-regulate or down-regulate Shoca expression. Generally, an agent capable of binding Shoca, modulating Shoca activity and/or modulating Shoca expression will be capable of modulating the wnt signalling pathway.

Any suitable format may be used for the assay. In general terms such screening methods may involve contacting a polypeptide of the invention with a test agent and monitoring for binding of the test agent to the polypeptide or measuring Shoca activity. A polypeptide of the invention may be incubated with a test agent. Modulation of Shoca activity may be determined. In a preferred aspect, the assay is a cell-based assay. Preferably the assay may be carried out in a single well of a microtitre plate. Assay formats which allow high throughput screening are preferred.

Modulator activity can be determined by contacting cells expressing a polypeptide of the invention with an agent under investigation and by monitoring an effect mediated by the polypeptide. The cells expressing the polypeptide may be in vitro or in vivo. The polypeptide of the invention may be naturally or recombinantly expressed. Preferably, the assay is carried out in vitro using cells expressing recombinant polypeptide. Preferably, control experiments are carried out on cells which do not express the polypeptide of the invention to establish whether the observed responses are the result of activation of the polypeptide. Typically the cells will express other molecules of the wnt signalling pathway such as β-catenin, LEF and/or TCF.

A method of identifying an agent capable of modulating the wnt signalling pathway, may consist essentially of:

(i) providing a polypeptide of the invention or a polynucleotide of the invention encoding said polypeptide and a test agent;
(ii) contacting the polypeptide or polynucleotide and the test agent; and
(iii) monitoring any interaction between the polypeptide or polynucleotide and the test agent, thereby determining whether the test agent is capable of modulating the Wnt signalling pathway.

An interaction between the polypeptide or polynucleotide and the test agent may be monitored directly by monitoring binding of the polypeptide or polynucleotide to the test agent. Preferably direct binding of the test agent to the polypeptide or to the mRNA encoding the polypeptide is monitored. For example, a radiolabelled test agent can be incubated with the polypeptide of the invention and binding of the test agent to the polypeptide can be monitored.

Assays may be carried out using cells expressing Shoca, and incubating such cells with the test agent. The results of the assay are compared to the results obtained using the same assay in the absence of the test agent. Cells expressing Shoca constitutively may be provided for use in assays for Shoca function. Alternatively, an interaction between the polypeptide or polynucleotide and the test agent may be monitored indirectly by monitoring activity of a Shoca polypeptide of the invention. An agent capable of modulating the wnt signalling pathway may be an inhibitor of Shoca activity or may be an activator of Shoca activity.

Shoca activity may be determined by monitoring an effect of stimulation or inhibition of Shoca activity on cells, for example by monitoring cell proliferation, differentiation, growth or survival.

Shoca activity may be determined by monitoring phosphorylation of a polypeptide of the invention and determining whether the test agent inhibits or enhances phosphorylation.

Shoca binds directly or indirectly to LEF/TCF transcription factors and/or co-associates with β-catenin in the nucleus. Shoca may repress or activate β-catenin-LEF/TCF mediated transcription in the nucleus depending on the cellular context. For Shoca to exert an effect on such transcription it must be present in the nucleus. Therefore, Shoca activity may be determined by monitoring the intracellular location of a polypeptide of the invention, and in particular translocation to the nucleus.

A method of the invention may be used to identify an agent which inhibits or enhances binding of Shoca to a molecule of the wnt signalling pathway such as β-catenin, LEF and/or TCF. A method of identifying an agent capable of modulating the wnt signalling pathway according to the invention may further comprise providing a molecule of the wnt signalling pathway capable of interacting with Shoca. The polypeptide or polynucleotide and the test agent and the wnt signalling molecule may then be contacted under conditions suitable for the interaction of the polypeptide and the wnt signalling molecule and the effect of the test agent on the interaction of the polypeptide and the wnt signalling molecule may be determined by monitoring the interaction. Preferably the wnt signalling molecule is β-catenin, TCF, LEF or any combination of β-catenin, TCF or/and LEF.

Substances that inhibit the interaction of a Shoca polypeptide of the invention with a wnt signalling molecule such as β-catenin, LEF or TCF may also be identified through a mammalian 2-hybrid assay, yeast 2-hybrid assay, yeast 3-hybrid assay (protein-DNA interaction assay) or other protein interaction assay such as a co-immunoprecipitation or an ELISA based technique.

Agents capable of modulating the wnt signalling pathway may be identified by determining whether a test agent inhibits or enhances modulation of gene transcription by a Shoca polypeptide of the invention. The effect of a test agent on Shoca-mediated repression or activation of gene expression may thus be monitored in a method of the invention. Typically, a reporter gene construct comprising a reporter gene under the transcriptional control of LEF and/or TCF is provided and contacted with a polypeptide of the invention and a test agent under conditions suitable for expression of a reporter gene. Expression of the reporter gene may be monitored and compared to expression in a control experiment without the test agent to determine whether the test agent modulates Shoca activity.

Assays may also be carried out to identify agents which modify Shoca expression, for example substances which up- or down-regulate expression. Generally, in such assays a polynucleotide of the invention is contacted with the test agent. The polynucleotide may be mRNA and the test agent may modulate translation. Preferably the polynucleotide is DNA and the test agent preferably modulates transcription. Such assays may, alternatively, be carried out for example by using antibodies for Shoca to monitor levels of Shoca expression.

Additional control experiments may be carried out.

Suitable test agents which can be tested in the above assays include combinatorial libraries, defined chemical entities and compounds, peptide and peptide mimetics, oligonucleotides and natural product libraries, such as display (e.g. phage display libraries) and antibody products.

Typically, organic molecules will be screened, preferably small organic molecules which have a molecular weight of from 50 to 2500 daltons. Candidate products can be biomolecules including, saccharides, fatty acids, steroids, purines, pyrimidines, derivatives, structural analogs or combinations thereof. Candidate agents are obtained from a wide variety of sources including libraries of synthetic or natural compounds. Known pharmacological agents may be subjected to directed or random chemical modifications, such as acylation, alkylation, esterification, amidification, etc. to produce structural analogs.

Test agents may be used in an initial screen of, for example, 10 agents per reaction, and the agents of these batches which show inhibition or activation tested individually. Test agents may be used at a concentration of from 1 nM to 1000 µM, preferably from 1 µM to 100 µM, more preferably from 1 µM to 10 µM. Preferably, Shoca activity in the presence of a test agent is compared to the activity shown in the absence of the test agent. A test agent which acts as an inhibitor may produce a 50% inhibition of Shoca activity. Alternatively a test agent which acts as an activator may enhance Shoca activity by 50%.

The activity of Shoca on β-catenin-LEF/TCF transcriptional activity is tissue-specific. For example, in thymic epihelial cells Shoca acts to repress such transcriptional activity but in fibroblasts Shoca stimulates transcription of gene sequences under the control of LEF/TCF. In one embodiment the present invention provides a method for identifying a cellular component that interacts with Shoca and which is responsible for determining the tissue-specific activity of Shoca. Such a method typically comprises any assay described herein for the identification of a modulator of the wnt signalling pathway in which the test agent is a cellular component. Suitable test agents include for example, a crude cellular extract, a fraction of a cellular extract, proteins purified from a cellular extract or a protein isolated from the cell type or tissue of interest.

Another aspect of the present invention is the use of polynucleotides encoding the Shoca polypeptides of the invention to identify mutations in Shoca genes which may be implicated in human disorders and, in particular, susceptibility to cancer. Identification of such mutations may be used to assist in diagnosis or susceptibility to such disorders and in assessing the physiology of such disorders. Polynucleotides may also be used in hybridisation studies to monitor for up- or down-regulation of Shoca expression. Polynucleotides such as SEQ ID NO: 1, SEQ ID NO: 3, SEQ ID NO: 5, SEQ ID NO: 7 or fragments thereof may be used to identify allelic variants, genomic DNA and species variants.

Diagnosis

The present invention provides a method for detecting variation in the expressed products encoded by Shoca genes. This may comprise determining the level of Shoca expressed in cells or determining specific alterations in the expressed product. Sequences of interest for diagnostic purposes include, but are not limited to, the conserved portions as identified by sequence similarity and conservation of intron/exon structure. The diagnosis may be performed in conjunction with kindred studies to determine whether a mutation of interest co-segregates with disease phenotype in a family.

The present inventors have shown that Shoca is expressed in many different cell types and neoplastic tissues. In particular, Shoca is involved in distinct tumour types including breast cancer, colon cancer and cervical cancer. Normal tissue from a broad range of organs was found to be either negative for Shoca or to express low levels of Shoca while expression of Shoca in these tissues was associated with less malignant tumour forms. Further, cancerous progression was shown to coincide with a loss of Shoca expression in many tumours. Accordingly, Shoca is a clinically relevant prognostic marker for tumours, especially breast, colon and cervical tumours. Shoca may also be used as a diagnostic maker for diseases which involve benign tissue changes such as mastopathy, apocrine metaplasia, intraductal hyperplasia, papilloma and carcinoma.

Thus in a further embodiment, the present invention provides a method of diagnosing cancer by determining the level of Shoca expression in a tissue sample from a subject. The invention also provides a method of predicting the progression of a tumour by determining the level of Shoca expression in a tissue sample from a subject. Also provided is a method of diagnosing a disease involving benign tissue changes such as mastopathy, apocrine metaplasia, intraductal hyperplasia, papilloma and carcinoma by determining the level of Shoca expression in a tissue sample from a subject. The level of Shoca expression may be determined by monitoring the level of a polypeptide of the invention or mRNA encoding a polypeptide of the invention. Any suitable tissue sample may be used, for example a biopsy or resection. Preferably the cancer is breast, colon or cervical cancer.

The expression of a Shoca protein or mRNA may be determined using an agent that interacts with Shoca. Suitable agents may be identified using a screening assay of the invention. Preferably, the agent is capable of binding specifically to the Shoca protein. More preferably the agent is an antibody of the invention.

A method of diagnosing cancer, or of predicting the progression of a tumour, or of diagnosing a disease involving benign tissue changes such as mastopathy, apocrine metaplasia, intraductal hyperplasia, papilloma and carcinoma may comprise the steps of:
(i) identifying an agent capable of interacting with Shoca;
(ii) contacting a sample from a human or animal subject with the agent;
(iii) monitoring binding of the agent to the sample; and
(iv) determining whether the level of Shoca expression is elevated or reduced in said sample compared to the level of Shoca expression in a sample from a human or animal subject not having cancer or said disease.

Diagnostic procedures may be performed on polynucleotides isolated from an individual or alternatively, may be performed in situ directly upon tissue sections (fixed and/or frozen) of patient tissue obtained from biopsies or resections, such that no nucleic acid purification is necessary. Appropriate procedures are described in, for example, Nuovo, G. J., 1992, "PCR In Situ Hybridization: Protocols And Applications", Raven Press, NY. Such analysis techniques include, DNA or RNA blotting analyses, single stranded conformational polymorphism analyses, in situ hybridization assays, and polymerase chain reaction analyses. Such analyses may reveal both quantitative aspects of the expression pattern of Shoca and qualitative aspects of Shoca expression and/or composition.

Alternative diagnostic methods for the detection of Shoca nucleic acid molecules may involve their amplification, e.g. by PCR (the experimental embodiment set forth in U.S. Pat. No. 4,683,202), ligase chain reaction (Barany, 1991, *Proc. Natl. Acad. Sci. USA* 88:189–193), self sustained sequence replication (Guatelli et al., 1990, *Proc. Natl. Acad. Sci. USA* 87:1874–1878), transcriptional amplification system (Kwoh et al., 1989, *Proc. Natl. Acad. Sci. 15 USA* 86:1173–1177), Q-Beta Replicase (Lizardi et al., 1988, *Bio/Technology* 6:1197) or any other nucleic acid amplification method (for example, Holland et al., 1991, *Proc. Natl. Acad. Sci. USA* 88:7276–7280), followed by the detection of the amplified molecules using techniques well known to those of skill in the art. These detection schemes are especially useful for the detection of nucleic acid molecules if such molecules are present in very low numbers.

Particularly suitable diagnostic methods are chip-based DNA technologies such as those described by Hacia et al., 1996, *Nature Genetics* 14:441–447, Shoemaker et al., 1996, *Nature Genetics* 14:450–456 and Welford et al., 1998, *Nucl. Ac. Res.* 26: 3059–3065. Briefly, these techniques involve quantitative methods for analyzing large numbers of nucleic acid sequence targets rapidly and accurately. By tagging with oligonucleotides or using fixed probe arrays, one can employ chip technology to segregate target molecules as high density arrays and screen these molecules on the basis of hybridization.

Following detection, the results seen in a given patient may be compared with a statistically significant reference group of normal patients and patients that have cancer. In this way, it is possible to correlate the amount or kind of Shoca encoded product detected with various cancers or predisposition to various cancers. Generally, only low levels of Shoca expression or no Shoca expression is seen in tissue from individuals not having a tumour so expression in such a tissue may be an indication of a cancerous tumour.

In an individual known to have a tumour, expression of Shoca may typically indicate that the tumour is not very aggressive and no expression of Shoca in the tumour cells may typically indicate that the tumour is malignant.

Therapeutic Treatment

The present invention also provides a method of treating a cancer in an individual, the method comprising:
(i) carrying out a method of diagnosis according to the invention on a tissue sample from the individual; and
(ii) administering an anti-cancer agent to the individual.

Another aspect of the present invention is the use of the agents that have been identified by screening techniques referred to above in the treatment of disease states which are responsive to regulation of Shoca activity, such as cancers. In particular, such substances may be used in the treatment of colon, breast and cervical cancers. The treatment may be therapeutic or prophylactic.

Accordingly, the present invention provides an agent capable of modulating the wnt signalling pathway identified by a method of the invention for use in a method of treatment by the human or animal body by therapy or in a method of diagnosis carried out on the human or animal body. The use of an agent identified by a method of the invention in the manufacture of a medicament for use in the diagnosis or treatment of cancer is also provided.

A method of treating cancer according to the invention may consist essentially of the steps of:
(i) identifying an agent capable of modulating Shoca activity; and
(ii) administering a therapeutically effective amount of the agent to a human or animal subject in need thereof.

A human or animal subject in need of treatment may be identified by a method of diagnosis according to the invention.

A therapeutically effective amount of an agent is an amount which when administered to a patient with cancer, improves the condition of a patient. The condition of a patient may be improved if one or more symptom of cancer is allieviated. The agent may, for example, kill tumour cells or inhibit tumour progression.

Agents identified according to the screening methods outlined above may be formulated with standard pharmaceutically acceptable carriers and/or excipients as is routine in the pharmaceutical art. For example, a suitable agent may be dissolved in physiological saline or water for injections. The exact nature of a formulation will depend upon several factors including the particular agent to be administered and the desired route of administration. Suitable types of formulation are fully described in Remington's Pharmaceutical Sciences, Mack Publishing Company, Eastern Pennsylvania, 17th Ed. 1985, the disclosure of which is included herein of its entirety by way of reference.

The agents may be administered by enteral or parenteral routes such as via oral, buccal, anal, pulmonary, intravenous, intra-arterial, intramuscular, intraperitoneal, topical or other appropriate administration routes.

A therapeutically effective amount of a modulator is administered to a patient. The dose of a modulator may be determined according to various parameters, especially according to the substance used; the age, weight and condition of the patient to be treated; the route of administration; and the required regimen. A physician will be able to determine the required route of administration and dosage for any particular patient. A typical daily dose is from about 0.1 to 50 mg per kg of body weight, according to the activity of the specific modulator, the age, weight and conditions of the subject to be treated, the type and severity of the degeneration and the frequency and route of administration. Preferably, daily dosage levels are from 5 mg to 2 g.

Nucleic acid encoding a Shoca polypeptide of the invention which inhibits or enhances Shoca activity or antisense nucleic acid may be administered to the mammal. Nucleic acid, such as RNA or DNA, and preferably, DNA, is provided in the form of a vector, such as the polynucleotides described above, which may be expressed in the cells of the mammal.

Nucleic acid administered to the mammal for gene therapy may encode a variant of Shoca with an impaired function such as a dominant negative mutant that disrupts the function of endogenous Shoca or may encode a constitutively active variant of Shoca that enhances the function of endogenous Shoca.

Nucleic acid encoding the polypeptide may be administered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 μg nucleic acid for particle mediated gene delivery and 10 μg to 1 mg for other routes.

The following Examples illustrate the invention.

EXAMPLE 1

Shoca-1, a Novel Gene Involved in Wnt-mediated Signalling

We have recently identified in mouse and human tissue a novel gene whose product is directly involved in wnt-mediated signalling. The gene (SEQ ID NO: 1 and SEQ ID NO: 3) encodes an SH2-domain containing adaptor protein of 52 kDa (as demonstrated by Western blotting) and has thus been designated Shoca-1. Subsequently, a second Shoca-like gene has been identified by use of EST analysis in the public domain (SEQ ID NO: 5). Neither existence nor function of these genes have yet been reported in any species.

Mouse Shoca-2 was found by doing a blast search in the EST database using the mouse Shoca-1 cDNA sequence. Using the partial EST sequences, 5' and 3' RACE was performed in order to obtain the full coding sequence. Since then a full length cDNA has been submitted to the public databases with a sequence identical to mouse Shoca-2 (accession code AK008803). Similarly, human Shoca-2 was found by BLAST search of the human EST and the human genome databases. Human Shoca-2 is found in the EST database (accession code AK024799). The human Shoca-2 sequence is entirely taken from the EST database.

The chromosomal localisations in human are 10q22-q23.1 for human Shoca-1 and 8pter-p23.3 for human Shoca-2. In addition, a fragmented DNA sequence corresponding to the N-terminal part of mouse Shoca-1 was found in the public domain. However, an error in the open reading frame of this sequence introduced a translation error. By correcting this error (one base pair) an amino acid sequence of 214 residues could correctly be translated.

There is a splice variant for mouse Shoca-1 which has an alternative exon 1 and hence a different amino acid sequence at the N-terminus of the protein. So far no evidence that this variant exists in human (based on the genomic sequence in the Shoca-1 region) has been determined and it is not known if it has any biological function. The mouse and human Shoca-2 differ by a stretch of a few amino acid residues which seem to be coded in a single exon (based on the human genomic sequence). This sequence has some interesting Prosite motifs. So far it is not know if this exon is included in certain mouse transcripts or if it is lacking in certain human transcripts.

The Shoca family is well conserved between mouse and man over the entire sequence revealing a sequence homology between mouse and man of approximately 90% for Shoca-1 and 70% for Shoca-2. The amino acid sequence between the orthologs of mouse and humans displays a 91% homology and 95% similarity (FIG. 4). We have also detected in zebra fish (D. rerio) two Shoca family members (for which there are presently only EST sequences known with accession codes AW419549 and BE016614, respectively). The N-terminal and the C-terminal sequences, where available, of mouse, man and zebra fish are strikingly similar, thus revealing well conserved domains of possibly distinct function(s) (FIGS. 2 and 3). Although bearing an SH2 motif, Shoca-1 is almost exclusively expressed in the nucleus. Mutants of Shoca-1 missing the first N-terminal 50 amino-acids fail to translocate from the cytoplasm to the nucleus, suggesting that a motif within this sequence contains the information for nuclear localization. Predictions have revealed that position 56–63 of SEQ ID NO:4 or 9 (PPKTKRAA) to over 30% probability contains the NLS in human Shoca-1.

EXAMPLE 2

Generation of Shoca Specific Antibodies

Antibody Preparation A

The anti Shoca-1 antibodies (rabbit polyclonal serum) used to determine the subcellular localization were generated in our Institute. Different batches were used whereby the animals were bled at different times after repetitive boosting. The immunogen was a mouse Shoca-1 derived peptide (SEQ ID NO:19) coupled to the carrier protein KLH
Peptide Shoca#0: $NH_2$-CLPDTSPPSPLTGPDRTWER-PLRC-$CONH_2$ This peptide represents a stretch of 22 amino acids corresponding to the mouse Shoca-1 residue positions 272 through 293. The N-terminal and C-terminal cysteines were introduced to allow loop formation on the protein carrier in order to enhance immunization.

Antibody Preparation B

The anti Shoca-1 antibodies that have been used in the staining experiments in Example 5 were generated in two rabbits by Eurogentec and also represent polyclonal preparations. All preparations used in stainings were affinity-purified using a peptide loaded column. The serum purified was derived from a single animal following the fourth booster immunization. The immunogens represent a mixture of two mouse Shoca-1 derived peptides (SEQ ID NOS: 20–21, respectively) coupled to the carrier protein KLH and were injected concomitantly:
Peptide Shoca#1: $NHCOCH_3$-CGEGPGDKPYEEISEEC-COOH
Peptide Shoca#2: $NHCOCH_3$-ADEERSRRAQRARDEY-RRC-$CONH_2$ Peptide#1 represents stretch 83 through 97 of mouse Shoca-1 protein sequence, 15 amino acid residues and peptide#2 represents stretch 220 through 237 of mouse Shoca-1 protein sequence, 18 amino acid residues. The N-terminal (for peptide#1) and C-terminal (for both peptides) cysteines were introduced to allow loop formation on the protein carrier for immunization (peptide #1) or to introduce a C-terminal anchoring residue in peptide #2. Both peptides were coupled onto carrier proteins and injected into rabbits concomitantly.

Antibody Preparation C

The human specific anti Shoca-1 antibodies were generated in rabbits by Eurogentec and do also represent a polyclonal preparation. The immunogen represents a human Shoca-1 derived peptide (SEQ ID NO:22) coupled to the carrier protein KLH taking advantage of cysteines added to the specific Shoca sequence N- or C-terminally and the heterobifunctional crosslinker MBS. Peptide-KLH conjugates were injected subcutaneously:
Peptide Shoca#3: $NHCOCH_3$-CGLRPPKTKRAASD-KHIQC-COOH Peptide#3 represents the 17 amino acid residues from position 53 through 69 of the human Shoca-1 protein sequence. The preparation used in staining experiments was affinity-purified using a peptide-loaded column as described below. The purified serum was derived from a single animal following the fourth booster immunisation.

Crude antisera were filtered through 0.45 µm filters and affinity-purified on peptide columns. The free peptide, with which animals were immunised, was covalently bound to iodoacetyl-coupled crosslinked agarose via its free sulfhydryl groups (SulfoLink Coupling Gel, Pierce #20401). Unbound reactive iodacetyl groups were quenched with cysteine. Antisera of the respective reactivity were allowed to bind to the peptide-columns. The column-bound fraction was eluted with 0.1 M Glycine, pH 3.0. The eluate was immediately neutralised with 1 M Tris-HCl to achieve pH 7.0. The purified antibodies were equilibrated against PBS (pH 7.3) and concentrated in 50 kD MWCO columns (Vivascience #VS0131). The protein concentration was determined using the BCA method (Pierce #23223/23224) using purchased rabbit IgG as concentration standards (Peprotech #500-P00). The final preparation was stabilised by adding 0.02% NaN3. The serum purified derived from a single animal following the fourth booster immunisation.

Antibody Preparation D

The SH2 domain specific anti Shoca-1 antibodies were generated and affinity-purified as described for antibody preparation C above except that a C-terminal cysteine was introduced as an anchoring residue. SEQ ID NO:23
Peptide Shoca#4: $NHCOCH_3$-DASGDFYSFLGVDPN-RHC-$CONH_2$ Peptide#4 represents the 17 amino acid residues from position 376 through 392 of the human Shoca-1 protein sequence. This sequence stretch is identical in human and mouse Shoca-1. The peptide was coupled to a carrier protein as described above and injected into rabbits.

Antibody Preparation E

The human specific anti Shoca-2 antibodies were generated and affinity-purified as described for antibody preparation D. SEQ ID NO:24
Peptide Shoca#5: $NHCOCH_3$-QQMLADSINRMKC-$CONH_2$ Peptide#5 represents the 12 amino acid residues from position 181 through 192 of the human Shoca-2 protein sequence. This sequence has neither sequence identity with human Shoca-1 nor with mouse Shoca-1 or -2. The peptide was coupled to a carrier protein and injected into rabbits.

Verification of Antibody Preparations

Western blot analysis was performed on various cell and protein material in order to verify the specificity of the antibody preparations. In particular, a blot was analysed with antibody preparation B. HEK293 cells transfected with various mouse Shoca-1 constructs namely 1. HEK293 with control plasmid; 2. HEK293 transfected with mouse Shoca-1 untagged; 3. HEK293 transfected with mouse Shoca-1 C-terminal HA-tag; and 4. HEK293 untransfected.

Antibody preparation B: Single bands corresponding to untagged and HA tagged Shoca-1 were seen in mouse Shoca-1 transfected HEK293 cells (data not shown).

Antibody preparation C: A single band is seen in the nuclear fraction of the human tumour cell line NCI-H520 at the correct molecular weight. No band was detected when staining mouse TEC cells verifying that this preparation is human specific.

Antibody preparation D: Nuclear detection of Shoca-1 in mouse TEC cells was carried out using a blot with antibody preparation D. Cytoplasmic and nuclear fractions of mouse thymic epithelial cells were used: 1. TEC1-2, cytoplasmic; 2. TEC1-2 nuclear (data not shown). Staining of recombinantly expressed mouse Shoca-1 SH2 domain. A blot with anti-penta His antibodies and antibody preparation D respectively were carried out. Bacterial expression of mouse Shoca-1 SH2 domain (14.5 kDa including His tag) was identified, with higher levels being detected 5 hr after induction in the supernatant: 1. supernatant collected 3 hr after induction; 2. supernatant collected 5 hr after induction; 3. pellet collected 5 hr after induction (data not shown). Specificity for other SH2 domain proteins has been tested. GST fused Grb2-SH2 was not stained with antibody preparation D whereas the control anti-GST gave a nice band.

The western blot analysis were performed according to the following protocol. For total lysate, cells were suspended in lysis buffer (75 mM Tris pH8.0; 100 mM NaCl, 1% NP-40, 0.1 mM AEBSF and a protease inhibitor-mix) and centrifuged to remove debris. Supernatants were collected and same protein amounts were subjected to SDS-PAGE on 10% Bis/Tris gels under reducing conditions. Proteins were transferred onto PVDF membrane by semi-dry blotting (buffer: 25 mM Tris, 0.2M glycin, 20% ethanol). Membranes were blocked with 5% milk powder in TBST before incubation with affinity purified anti-Shoca antibodies (100–200 ng/ml). After 3 washes in TBST, membranes were incubated with HRP-coupled anti-rabbit-Ig antibodies (Amersham/Pharmacia) at a dilution of 1:2000. Finally, membranes were washed and developed by ECL-plus (Amersham/Pharmacia) chemiluminescence. For cytosolic versus nuclear lysates, cells were swollen for 15 min on ice in lysis buffer A (10 mM Hepes, 10 mM KCl, 0.1 mM EDTA, 1 mM EGTA, 1 mM DTT, protease inhibitor-mix). NP-40 was then added to a final concentration of 0.6% immediately followed by vortexing for 10 seconds and centrifugation for 30 seconds. The supernatant was referred to as cytosolic extract. The pellet was washed once in buffer A, resuspended in buffer B (20 mM Hepes, 0.4 M NaCl, 1 mM EDTA, 1 mM EGTA, 1 mM DTT, protease inhibitor-mix) and vortexed for 30 min at 4° C. After centrifugation for 5 min the supernatant was recovered as nuclear extract.

EXAMPLE 3

Shoca-1 and Shoca-2 Expression Profile

Figure 6A:
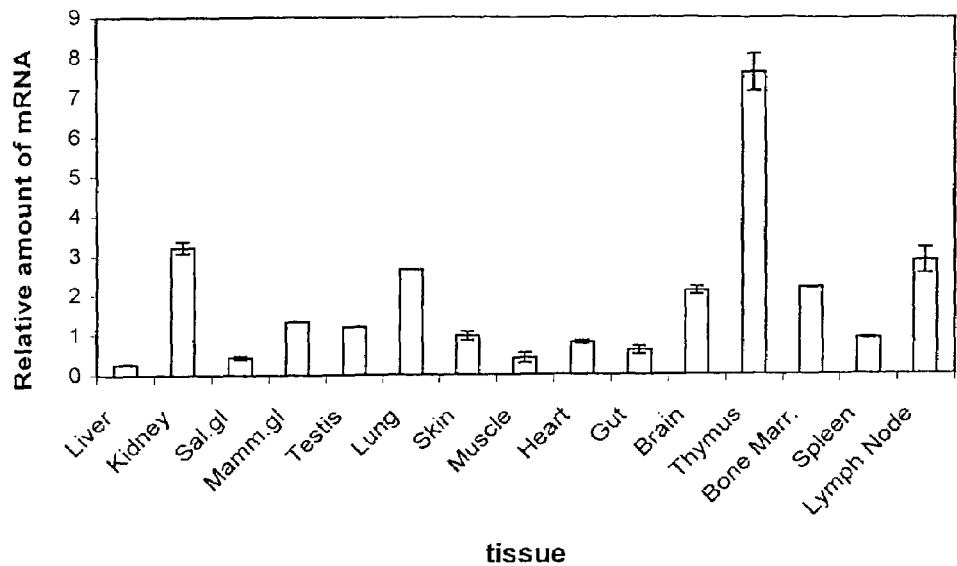
FIG. 6 shows Shoca-1 (FIG. 6A) and Shoca-2 (FIG. 6B) expression profiles in adult C57B6 mouse tissues analysed using a TaqMan assay.
Figure 6B:
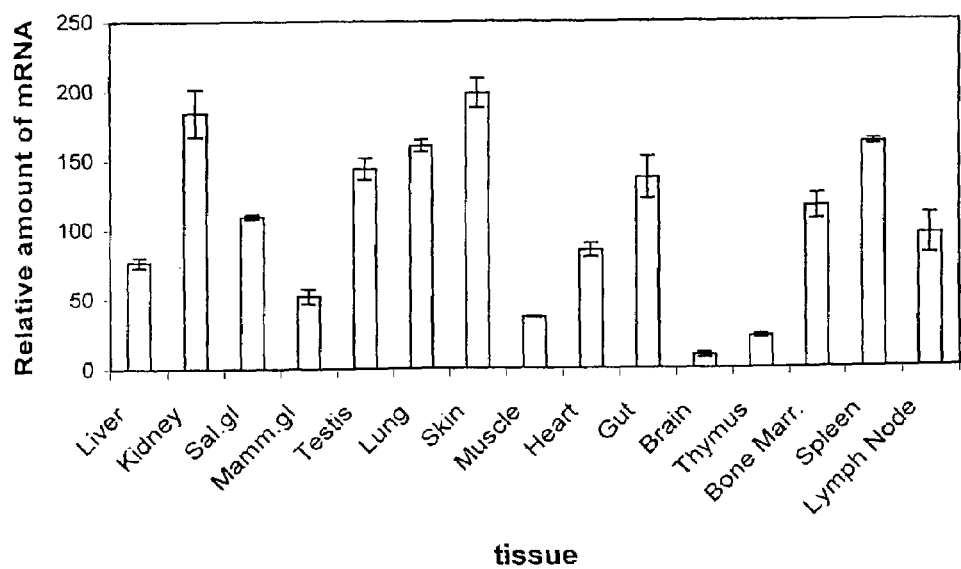

Shoca-1 is expressed in mice in thymic epithelial cells as early as the first detection of a thymic anlage and is also present in thymi of nude mice. Thus, Shoca-1 expression is independent of thymic lymphopoiesis and in particular the structured cross-talk between thymocytes and thymic epithelial cells. Shoca-1 expression has also been detected in bone marrow and in particular in stroma cells known to support hematopoiesis. Brain, kidney, and lung constitute other sites where Shoca-1 is expressed at low abundancy when assayed by PCR (FIG. 6), although Northern blotting was insufficiently sensitive to detect specific transcripts. By contrast, Shoca-2 expression is much more commonly expressed in different tissues (FIG. 6).

EXAMPLE 4

Figure 7:
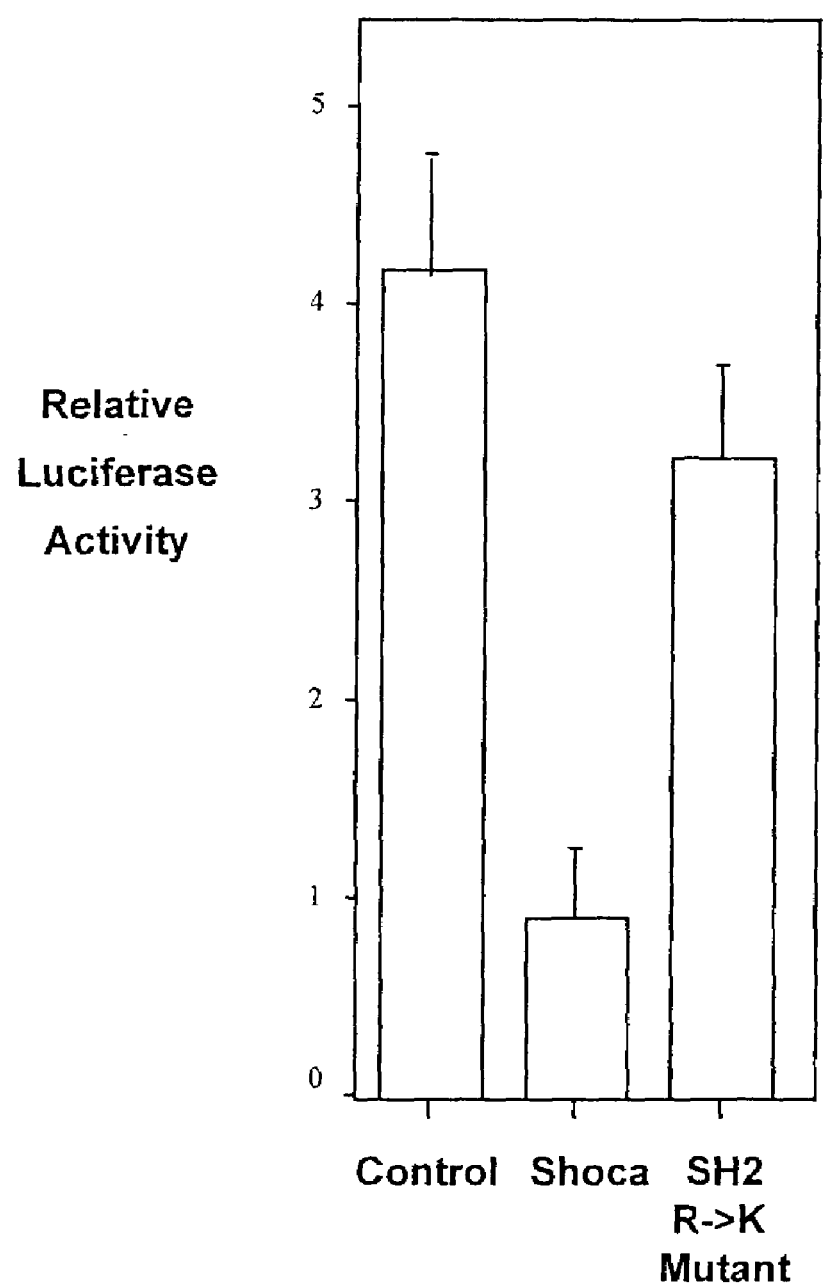
FIG. 7 shows the results of a luciferase reporter gene assay demonstrating that Shoca-1 modulates the transcriptional activation of β-catenin-LEF/TCF regulated activation. Expression of wild-type mouse Shoca-1 suppresses the spontaneous activity of a reporter gene while a mutant (R-K) disabling the SH2 domain fails to exert a suppressive effect depending on the cellular context.

Functional Studies Reveal Epistatic Placement of Shoca-1 in the Wnt/β-catenin Signalling Pathway The functional in vitro analysis of Shoca-1 has revealed that its expression in thymic epithelial cells represses the transcriptional activation of β-catenin-LEF/TCF regulated activation of a reporter gene. This suppression is dependent on a functional SH2-domain as a point mutation in that domain ablates any repressive function (FIG. 7). Arg350 (of mouse Shoca-1) in the SH2 domain was changed to a lysine residue. This arginine is located in the pTyr pocket and is critical for the SH2 domain function (Sawyer, 1998, *Biopolymers* 47: 243–261). It forms important contacts with the phosphate oxygen of the pTyr side chain of pTyr containing ligands to the SH2 domain. Overexpression of the R/K mutant of Shoca-1 has furthermore been associated with a decreased cellular proliferation. Electric mobility shift assays using Shoca-1 specific antibodies revealed that Shoca-1 is complexed with LEF/TCF.

This finding has been further confirmed in independent experiments where DNA sequences encoding the TCF-binding sequences could trap Shoca-1 from nuclear extracts. In these experiments, a biotinylated dsDNA adaptor containing a TCF binding site was incubated with nuclear extract from murine TEC 1-2 cells. The adaptor (and hence proteins complexed to the TCF binding site) was captured using paramagnetic streptavidin beads. The beads were washed, mixed with protein sample buffer, loaded on a PAGE gel and blotted onto a nitrocellulose membrane. Western analysis was then performed using polyclonal rabbit anti-Shoca antibody as a primary antibody.

The interaction with a transcriptionally active complex containing not only LEF/TCF but also β-catenin is further corroborated by confocal microscopy which shows that Shoca co-localizes with β-catenin in the nucleus. In addition, increased phosphorylation is observed of Shoca-1 after Li stimulation. This was demonstrated by incubating murine TEC 1-2 cells with medium containing 20 mM lithium for different timepoints, immunoprecipitating Shoca-1 using polyclonal rabbit anti-Shoca antibody, separating the proteins on a PAGE gel and probing with a phosphotyrosine specific antibody in a Western analysis.

All in all, these data support a very central and epistatic placement of the Shoca proteins in the Wnt/β-catenin signalling pathway. In contrast to the observations in thymic epithelial cells, Shoca-1 overexpression in fibroblast stimulates LEF/TCF-dependent transcription of a reporter gene thus arguing for further tissue-specific molecules functionally and/or physically interacting with Shoca-1. Thus, Shoca-1 may effect a tissue specific repressor function in possible combination with a secondary molecule.

EXAMPLE 5

Tissue Restricted Expression and Role of Shoca in Oncogenesis

The major role of Wnt signalling in adult tissues is the regulation of cell proliferation. Constitutive mutations in APC or β-catenin lead to hyperproliferation and carcinogenesis. Results from screening arrays containing normal and malignant tissue from different human organs has revealed that a number of tumours mainly of epithelial cell origin express Shoca-1 (Table 1).

TABLE 1

Tissue micro array immunostaining for Shoca-1 expression

N = Number of samples that could be analysed
Score = Number of moderate to strong stainers divided by N
Percentage = Percentage value of score
Any score above 0.3 was taken as significant and marked with an asterisk

| Pathology | N | Neg. | Weak | Mod. | Strong | Score | Percentage |
|---|---|---|---|---|---|---|---|
| Adenomatoid tumor | 8 | 1 | 0 | 3 | 4 | 7/8 | 87.5% * |
| Adrenal gland, adenoma | 15 | 12 | 0 | 3 | 0 | 3/15 | 20.0% |
| Adrenal gland, cancer | 6 | 4 | 0 | 1 | 0 | 1/6 | 16.7% |
| Angiosarcoma | 3 | 0 | 1 | 1 | 1 | 2/3 | 66.7% * |
| Anus, squamous cell cancer | 5 | 3 | 0 | 2 | 0 | 2/6 | 40.0% |
| Astrocytoma | 34 | 23 | 1 | 8 | 2 | 10/34 | 29.4% |
| Benign histiocytoma | 26 | 5 | 5 | 6 | 10 | 16/25 | 61.5% * |
| Breast, apocrine cancer | 2 | 0 | 1 | 1 | 0 | 1/2 | 50.0% * |
| Breast, cribriform cancer | 8 | 5 | 1 | 2 | 0 | 2/8 | 25.0% |
| Breast, ductal cancer | 46 | 23 | 8 | 12 | 3 | 15/46 | 32.6% * |
| Breast, lobular cancer | 37 | 5 | 10 | 13 | 9 | 22/37 | 59.5% * |
| Breast, medullary cancer | 27 | 19 | 4 | 4 | 0 | 4/27 | 14.8% |
| Breast, mucinous cancer | 23 | 2 | 5 | 9 | 7 | 16/23 | 69.6% * |
| Breast, Phylloides tumor | 11 | 3 | 0 | 4 | 4 | 8/4 | 72.7% * |
| Breast, tubular cancer | 24 | 4 | 2 | 8 | 10 | 18/24 | 75.0% * |
| Carcinoid tumor | 33 | 29 | 2 | 2 | 0 | 2/33 | 6.1% |
| CML | 5 | 4 | 0 | 1 | 0 | 1/5 | 20.0% |
| Colon adenoma, mild dysplasia | 45 | 5 | 8 | 18 | 4 | 32/45 | 48.9% * |
| Colon adenoma, moderate dysplasia | 45 | 7 | 8 | 25 | 5 | 30/45 | 66.7% * |
| Colon adenoma, severe dysplasia | 44 | 17 | 5 | 22 | 0 | 22/44 | 50.0% * |
| Colon, adenocarcinoma | 45 | 33 | 5 | 7 | 0 | 7/45 | 15.6% |
| Craniophayryngeoma | 4 | 0 | 1 | 2 | 1 | 3/4 | 75.0% * |
| Dermatofibroma protuberans | 4 | 0 | 0 | 4 | 0 | 4/4 | 100.0% * |
| Endometrioid stroma sarcoma | 4 | 0 | 1 | 0 | 0 | 0/4 | 0.0% |
| Endometrium endometroid carcinoma | 47 | 35 | 6 | 4 | 2 | 6/47 | 12.8% |
| Endometrium, serous carcinoma | 19 | 9 | 3 | 6 | 1 | 9/19 | 36.8% * |
| Ependymoma | 7 | 0 | 1 | 4 | 2 | 6/7 | 85.7% * |
| Epitheloid Hemangioma | 1 | | | | | 1/1 | 0.0% |
| Epitheloid sarcoma | 2 | | | | | 2/2 | 0.0% |
| Esophagus, adenocarcinoma | 6 | 3 | 2 | 1 | 0 | 1/6 | 16.7% |
| Esophagus, small cell carcinoma | | | | | | | |
| Esophagus, squamous cell carcinoma | 34 | 24 | 3 | 7 | 0 | 7/34 | 20.6% |
| Esthesioneuroblastoma | 3 | 0 | 0 | 2 | 0 | 2/3 | 66.7% * |
| Fibrosarcoma | 8 | 3 | 1 | 4 | 0 | 4/8 | 50.0% * |
| Gall bladder, adenocarcinoma | 27 | 11 | 6 | 2 | 8 | 10/27 | 37.0%* |
| Ganglioneuroma | 7 | 0 | 3 | 3 | 1 | 4/7 | 57.1% * |
| GIST | 13 | 6 | 0 | 7 | 0 | 7/6 | 53.8%* |
| Glioblastoma multiforme | 45 | 24 | 6 | 8 | 7 | 15/45 | 33.3% * |
| Glomus tumor | 9 | 3 | 1 | 2 | 3 | 5/9 | 55.6% * |
| Granular cell tumor | 8 | 2 | 4 | 2 | 0 | 2/8 | 25.0% |
| Hemangiopericytoma | 16 | 4 | 2 | 3 | 3 | 6/16 | 37.5% * |
| Hepatocellular carcinoma | 46 | 40 | 3 | 3 | 0 | 3/46 | 6.5% |
| Hodgkin lymphoma, mixed cell | 15 | 8 | 3 | 4 | 0 | 4/15 | 26.7% |
| Hodgkin lymphoma, nodular sclerosis | 9 | 6 | 3 | 0 | 0 | 0/9 | 0.0% |
| Kapillary hemangioma | 26 | 2 | 3 | 3 | 18 | 21/26 | 80.8% * |
| Kaposi Sarcoma | 27 | 12 | 2 | 11 | 2 | 13/27 | 48.1% * |
| Kidney, chromophobic cancer | 14 | 12 | 0 | 2 | 0 | 2/14 | 14.3% |
| Kidney, clear cell cancer | 44 | 35 | 0 | 6 | 3 | 9/44 | 20.5% |
| Kidney, oncocytoma | 10 | 2 | 0 | 7 | 1 | 8/10 | 80.0% * |
| Kidney, papillary cancer | 43 | 29 | 6 | 3 | 5 | 8/43 | 18.6% |
| Larynx, squamous cell carcinoma | 40 | 7 | 5 | 20 | 8 | 28/40 | 70.0% * |
| Leiomyoblastoma | 7 | 4 | 0 | 3 | 3 | 6/7 | 85.7% * |
| Leiomyoma | 55 | 16 | 11 | 18 | 10 | 28/55 | 50.9% * |
| Leiomyosarcoma | 46 | 29 | 6 | 9 | 2 | 11/46 | 23.9% |
| Lipoma | 16 | 5 | 1 | 5 | 5 | 10/16 | 62.5% * |
| Liposarcoma | 23 | 7 | 8 | 4 | 4 | 8/23 | 34.8% * |
| Lung, adenocarcinoma | 44 | 21 | 11 | 9 | 3 | 12/44 | 27.3% |
| Lung, large cell cancer | 44 | 35 | 6 | 3 | 0 | 3/44 | 6.8% |
| Lung, small cell cancer | 43 | 37 | 3 | 3 | 0 | 3/43 | 7.0% |
| Lung, squamous cell carcinoma | 48 | 35 | 7 | 3 | 3 | 6/48 | 12.5% |
| Malignant fibrous histiocytoma | 26 | 13 | 4 | 7 | 2 | 9/26 | 34.6% * |
| Malignant mesothelioma | 25 | 14 | 6 | 2 | 3 | 5/25 | 20.0% |
| Malignant Schwanoma | 12 | 3 | 0 | 9 | 0 | 9/12 | 75.0% * |
| MALT lymphoma | 46 | 35 | 8 | 1 | 0 | 1/46 | 2.2% |
| Medulloblastoma | 4 | 3 | 0 | 1 | 0 | 1/4 | 25.0% |
| Meningeoma | 44 | 31 | 4 | 6 | 3 | 9/44 | 20.5% |
| Neurofibroma | 36 | 17 | 9 | 10 | 0 | 10/36 | 27.8% |
| NHL, diffuse large B | 22 | 17 | 3 | 1 | 1 | 2/22 | 9.1% |
| NHL, others | 28 | 19 | 6 | 9 | 0 | 9/28 | 32.1% * |
| Oligodendroglioma | 21 | 13 | 2 | 5 | 1 | 6/21 | 28.6% |
| oral cavity, squamous cell carcinoma | 49 | 18 | 13 | 18 | 0 | 18/49 | 36.7% * |

TABLE 1-continued

Tissue micro array immunostaining for Shoca-1 expression

N = Number of samples that could be analysed  
Score = Number of moderate to strong stainers divided by N  
Percentage = Percentage value of score  
Any score above 0.3 was taken as significant and marked with an asterisk

| Pathology | N | Neg. | Weak | Mod. | Strong | Score | Percentage |
|---|---|---|---|---|---|---|---|
| Ovarian cancer, other types | 12 | 4 | 1 | 7 | 0 | 7/12 | 58.3%* |
| Ovary, Brenner tumor | 8 | 5 | 0 | 3 | 0 | 3/8 | 37.5%* |
| Ovary, endometroid cancer | 31 | 14 | 6 | 9 | 2 | 11/31 | 35.5%* |
| Ovary, mucinous cancer | 14 | 4 | 0 | 3 | 7 | 10/14 | 71.4%* |
| Ovary, serous cancer | 43 | 17 | 6 | 15 | 5 | 20/43 | 46.5%* |
| Pancreas, adenocarcinoma | 43 | 28 | 4 | 8 | 3 | 11/43 | 25.6% |
| Paraganglioma | 10 | 10 | 0 | 0 | 0 | 0/6 | 0.0% |
| Parathyroid, adenoma | 26 | 9 | 0 | 17 | 0 | 17/26 | 65.4%* |
| Parathyroid, cancer | 2 | 0 | 0 | 2 | 0 | 2/2 | 100.0%* |
| Penile ca | 39 | 24 | 8 | 7 | 0 | 7/39 | 17.9% |
| Pharynx, lamphoepithelial cancinoma | 5 | 2 | 3 | 0 | 0 | 0/5 | 0.0% |
| Pheochromocytoma | 28 | 28 | 0 | 0 | 0 | 0/28 | 0.0% |
| PNET | 15 | 11 | 1 | 3 | 0 | 3/15 | 20.0% |
| Prostate cancer, hormon-refractory | 46 | 35 | 5 | 6 | 0 | 6/46 | 13.0% |
| Prostate cancer, untreated | 47 | 26 | 12 | 8 | 1 | 9/47 | 19.1% |
| Rhabdomyosarcoma | 13 | 6 | 1 | 4 | 2 | 6/13 | 46.2%* |
| Salivary gland, acinus cell cancer | 5 | 4 | 0 | 1 | 0 | 1/5 | 20.0% |
| Salivary gland, adenolymphoma | 26 | 3 | 4 | 17 | 2 | 19/26 | 73.1%* |
| Salivary gland, cylindroma | 44 | 9 | 13 | 17 | 5 | 22/44 | 50.0%* |
| Salivary gland, mucoepidermoid | 2 | 1 | 1 | 0 | 0 | 0/2 | 0.0% |
| Salivary gland, Pleomorphic adenoma | 43 | 3 | 7 | 11 | 22 | 33/43 | 76.7%* |
| Schwannoma | 39 | 31 | 3 | 4 | 1 | 5/39 | 12.8% |
| Skin, basalioma | 41 | 13 | 9 | 19 | 0 | 19/41 | 46.3%* |
| Skin, benign appendix tumor | 26 | 5 | 5 | 14 | 2 | 16/26 | 61.5%* |
| Skin, benign nevus | 45 | 16 | 7 | 20 | 2 | 22/45 | 48.9%* |
| Skin, malignant melanoma | 44 | 26 | 4 | 12 | 2 | 14/44 | 31.8% |
| Skin, Merkel cell cancer | 4 | 2 | 0 | 2 | 0 | 2/4 | 50.0%* |
| Skin, squamouse cell cancer | 39 | 10 | 9 | 18 | 2 | 20/39 | 51.3%* |
| Small intestine, ademocarcinoma | 9 | 3 | 1 | 4 | 1 | 5/9 | 55.6%* |
| Stomach, diffuse adenocarcinoma | 19 | 10 | 5 | 3 | 1 | 4/19 | 21.1% |
| Stomach, intestinal adenocarcinoma | 41 | 26 | 5 | 10 | 0 | 10/41 | 24.4% |
| Synovial sarcoma | 4 | 2 | 0 | 2 | 0 | 2/2 | 50.0%* |
| Tendon sheet, giant cell tumor | 32 | 5 | 13 | 13 | 1 | 14/32 | 43.8%* |
| Teratoma | 2 | 1 | 1 | 0 | 0 | 0/2 | 0.0% |
| Testis, non-seminomatous cancer | 45 | 19 | 13 | 7 | 6 | 13/45 | 28.9% |
| Testis, seminoma | 47 | 34 | 6 | 4 | 3 | 7/47 | 14.9% |
| Thymoma | 23 | 17 | 1 | 5 | 0 | 5/23 | 21.7% |
| Thyroid, adenoma | 43 | 17 | 15 | 10 | 1 | 11/43 | 25.6% |
| Thyroid, anaplastic cancer | 7 | 1 | 0 | 2 | 4 | 6/7 | 85.7%* |
| Thyroid, follicular cancer | 46 | 14 | 5 | 18 | 9 | 27/46 | 58.7%* |
| Thyroid, medullary cancer | 8 | 4 | 1 | 0 | 3 | 3/8 | 37.5%* |
| Thyroid, papillary cancer | 33 | 9 | 2 | 10 | 12 | 22/33 | 66.7%* |
| Urinary bladder cancer, cancer, TCC invasive | 41 | 26 | 10 | 5 | 0 | 5/41 | 12.2% |
| Urinary bladder cancer, TCC non-invasive | 40 | 22 | 8 | 8 | 2 | 10/40 | 25.0% |
| Urinary bladder, adenocarcinoma | 4 | 1 | 1 | 2 | 0 | 2/4 | 50.0%* |
| Urinary bladder, inverted papilloma | 1 | 0 | 0 | 1 | 0 | 1/1 | 100.0%* |
| Urinary bladder, sarcomatoid cancer | 6 | 2 | 2 | 2 | 0 | 2/6 | 33.3% |
| Urinary bladder, small cell cancer | 5 | 1 | 1 | 1 | 2 | 3/5 | 60.0%* |
| Urinary bladder, squamous cell cancer | 7 | 2 | 1 | 1 | 3 | 4/7 | 57.1%* |
| Urinary bladder, squamous cell carcinoma | 41 | 22 | 7 | 9 | 3 | 12/41 | 29.3% |
| Uterus, carcinsarcoma | 6 | 2 | 2 | 1 | 1 | 2/6 | 33.3%* |
| Uterus, cervix, adenocarcinoma | 2 | 0 | 0 | 2 | 0 | 2/2 | 100.0%* |
| Uterus, cervix, CIN III | 16 | 0 | 3 | 13 | 0 | 13/16 | 81.3%* |
| Vagina, squamous, cell cancer | 5 | 3 | 2 | 0 | 0 | 0/5 | 0.0% |
| Vulva, squamous, cell cancer | 39 | 14 | 11 | 13 | 1 | 14/39 | 35.9%* |

A set of tissue micro arrays (7 slides each) was analysed for Shoca expression. The set contained about 3000 tumours of 129 different tumour categories. Immunostaining was first optimised on test slides. The conditions described below were considered optimal. Then, all TMA slides used for this study were immunostained in one experiment. Only the negative control reaction was performed later (when reagents were provided). Immunostainings were done according to the following protocols:

Antibody: Shoca-1 specific type B
Slide pre-treatment: pronase, 15 min, 37° C.
Peroxidase blocking: 0.3% H$_2$O$_2$/Methanol, 30 minutes
Antibody dilution: 1:32'000
Incubation: overnight (4° C.)
Detection system: ABC; DAB
Positive control: thymus epithelial cells
Negative control: serum of the animal producing the antibody (after antibody extraction)

Using the conditions described above, the negative control reactions were completely negative while a staining of various intensities was observed for the Shoca-1 antibody in many tumours and normal tissues. All sections (stained and control sections) were reviewed by one pathologist on one day to maximise the internal consistency. For all tumour samples the fraction of positive cells were estimated and staining intensity was recorded according to a four step scale (0–3+). To categorise the tumours an arbitrarily selected system was used (Table 2).

TABLE 2

Categorisation of tumours

| Category | Definition |
|---|---|
| Negative | no staining |
| Weak | 0–50% of cells 1+ |
| Moderate | >50% 1+ or <50% 2+ |
| Strong | >50% 2+ or any 3+ staining |

The protein seems to be expressed in many different cell types and neoplastic tissues. It is possible that the protein is also expressed (at lower level) in tissues that were considered negative at the selected immunohistochemistry conditions. Despite all inherent shortcomings of immunohistochemistry, it can be expected that the different staining levels as determined on the tissue microarrays do at least represent true differences in the expression level of Shoca-1. This means, that tumours that are scored as 3+ will in general have a higher expression level than 2+ tumours, 2+ tumours will have a higher expression level than 1+ tumours, and 1+ tumours will express more Shoca-1 than tumours that are scored negative.

These data demonstrate the involvement of Shoca-1 in distinct tumour types including breast cancer, colon cancer and cervical cancer. A comprehensive analysis of the different tissues and tumour entities indicated further that normal tissue from a broad range of organs was low positive to negative for Shoca-1 while expression of this molecule was associated with less malignant tumour forms in these tissues. Moreover, cancerous progression coincided with a loss of Shoca-1 expression in many of the tumours (Table 3). This finding is particularly interesting as there is presently to our knowledge extremely few clinically relevant prognostic markers are available which are down-modulated or lost upon tumour progression in breast, colon and cervical cancer.

TABLE 3

Relationship of Shoca expression and malignancy

| Pathology | Score | Shoca positivity | |
|---|---|---|---|
| Colon adenoma, moderate dysplasia | 30/45 | 66.7% | |
| Colon adenoma, severe dysplasia | 22/44 | 50.0% | |
| Colon adenocarcinoma | 7/45 | 15.6% | |
| Dermatofibroma protuberans | 4/4 | 100% | |
| Malignat fibrous histiocytoma | 9/26 | 34.6% | |
| Breast tubular cancer | 18/24 | 75.0% | |
| Breast ductal cancer | 15/46 | 32.6% | |
| Uterus Cervix CIN III | 13/16 | 81.3 | |
| Uterus squamous cell carcinoma | 12/41 | 29.3 | |

EXAMPLE 6

Shoca Gene Expression in Human Malignancies

The role of Shoca-1 and Shoca-2 in malignancy was examined by a reverse transcription polymerase chain reaction (RT-PCR) in over 50 human cancer cell lines, representing various malignancies and different stages of cancer development.

The starting material was total RNA isolated from cultured cell lines by Qiagen Rneasy Total RNA isolation kit. Starting with 1 µg total RNA, random hexamers (Roche) were used to prime a reverse transcription reaction (Titan One Tube RT-PCR (Roche). cDNA was amplified in two rounds for both Shoca-1 and Shoca-2. In both primary PCR reactions, a full length amplicon was generated, and a portion of this was amplified in the secondary PCR reaction. The primers used are specified below:

TABLE 4

PCR primers

| Name | Nucleotide Position | Sequence (5'–3') |
|---|---|---|
| Primary PCR Primers for Shoca-1. | | |
| Shoca1 5' | | TGC TGC AGC AGA TCC TGC AC |
| Shoca1 3' | | CCT GAA GTA ACT CTC CTC C |
| Shoca_F1 | n258–278 | CCCTGGTGACAAGCCCTACGA |
| Shoca_R1 | n710–731 | ATAGCACGGAGCGAGTGGTGTC |
| Primary PCR Primers for Shoca-2 | | |
| Shoca2_F2 | 348–365 | TCA CTC TGA AGA ATT CAC |
| Shoca2_R2 | 1063–1046 | TGA GTG TGA GAA TTC CAT |
| Nested PCR primers for Shoca-2 Reactions | | |
| Shoca2_F3 | 511–528 | GAT CAC TCT CCA GTT CTT |
| Shoca2_R3 | 717–697 | GGA TTT TCG CAG AGA TGC CTG |

PCR products were separated by electrophoresis on a 0.8% agarose gel overnight and examined under UV light after staining with 0.5 μg/ml ethidium bromide. The table below details the findings. Results are given as Pos, where a band of the correct molecular weight was detected, and Neg, where no PCR product was detected.

TABLE 5

Shoca gene expression in various human cancer cells lines
Results for 20 of the 54 cell lines are listed. All the 34 remaining cell lines were negative for Shoca-1 and positive for Shoca-2.

| Name | Tumour Type | Shoca-1 | Shoca-2 |
|---|---|---|---|
| 1. T47 D/6 | Breast | NEG | POS |
| 2. PAN 02 | Pancreatic | NEG | NEG |
| 3. U-87 | Glioblastoma | NEG | POS |
| 4. T84 MCB | lung met from colon carcinoma | NEG | POS |
| 5. NCI-H520 | Squamous cell carcinoma lung | POS | POS |
| 6. KLE | Endometrial carcinoma | NEG | NEG |
| 7. SK-LU- 1 | Lung adenocarcinoma | N.D. | POS |
| 8. U-251 MG | Glioma | NEG | NEG |
| 9. NCI-H128. | SCLC met pleural effusion | NEG | NEG |
| 10. SCATT | Renal | NEG | POS |
| 11. NCI-H460 | Large cell lung carcinoma | NEG | POS |
| 12. LoVo | Colon met site supraclavicular | NEG | POS |
| 13. GLC-08 | SCLC | NEG | POS |
| 14. Hep G2 | Hepatocellular carcinoma | NEG | POS |
| 15. HT1376 | Urinary bladder carcinoma | NEG | POS |
| 16. N417 | Small Cell Lung | NEG | NEG |
| 17. LN Cap | Prostate | NEG | POS |
| 18. U105MG | Glioma | NEG | NEG |
| 19. SW 837 | Rectal adenocarcinoma | NEG | POS |
| 20. Colo 320 | Colon | NEG | NEG |
| 21. no template | | NEG | NEG |

The findings for Shoca-1 demonstrate that it is rarely expressed in human cancer cell lines, with only one (NCI H520) clearly positive. Shoca-2 was far more widely expressed in human tumours than Shoca-1. Only 7 cell lines were clearly negative of the 54 tested. These were PAN02, KLE, U251MG, NCIH128, N417, U105MG, and Colo320. These tumours cover 6 different tumour types, with only Gliomas represented twice. Another Glioma (U87), was positive for Shoca-2.

The invention claimed is:

1. An isolated Shoca-1 polypeptide comprising the amino acid sequence of SEQ ID NO:4.

2. An isolated Shoca-1 polypeptide consisting of the amino acid sequence of SEQ ID NO:4.

* * * * *

SEQUENCE LISTING

<160> NUMBER OF SEQ ID NOS: 32

<210> SEQ ID NO 1
<211> LENGTH: 1296
<212> TYPE: DNA
<213> ORGANISM: Mus musculus
<220> FEATURE: 24:<220
<221> NAME/KEY: CDS
<222> LOCATION: (1)..(1296)

<400> SEQUENCE: 1

```
atg ctg cag cag atc ctg cag gac atg tac atc gac ccg gag ctg ttg      48
Met Leu Gln Gln Ile Leu Gln Asp Met Tyr Ile Asp Pro Glu Leu Leu
1               5                   10                  15 gcc gag ctc agc gat gtg cag aag cac atc ctc ttc tat aag atg cga      96
Ala Glu Leu Ser Asp Val Gln Lys His Ile Leu Phe Tyr Lys Met Arg
            20                  25                  30 gag gag cag ctg cgg cga tgg agg gaa cgg gag gcg tgg gat gcc ctg     144
Glu Glu Gln Leu Arg Arg Trp Arg Glu Arg Glu Ala Trp Asp Ala Leu
        35                  40                  45 gct cag gca gag ggc ctg agg ccc gca aag gtc aag aga gcg agc aac     192
Ala Gln Ala Glu Gly Leu Arg Pro Ala Lys Val Lys Arg Ala Ser Asn
    50                  55                  60 aag cat ctc cag tgg ctt ctg gga gca gat ggt gag gtc tgg gtg tgg     240
Lys His Leu Gln Trp Leu Leu Gly Ala Asp Gly Glu Val Trp Val Trp
65                  70                  75                  80 gtc atg ggc gaa ggc cct gga gac aag ccc tac gaa gag ata tct gaa     288
Val Met Gly Glu Gly Pro Gly Asp Lys Pro Tyr Glu Glu Ile Ser Glu
                85                  90                  95 gaa ctg att gca gag agg gcc cgg ctg caa gca cag aaa gag gct gaa     336
Glu Leu Ile Ala Glu Arg Ala Arg Leu Gln Ala Gln Lys Glu Ala Glu
            100                 105                 110 gag ctc tgg aga cag aag gaa gca gag atc acc aag aag ttc cgg gat     384
```

```
                                                                    -continued Glu Leu Trp Arg Gln Lys Glu Ala Glu Ile Thr Lys Lys Phe Arg Asp
        115                 120                 125 gcc ttg gcc aat gag aaa gct cgg att ctg gca gag aag tgg aaa gtg      432
Ala Leu Ala Asn Glu Lys Ala Arg Ile Leu Ala Glu Lys Trp Lys Val
130                 135                 140 gag atg gag gac cgc aag gct gct aaa att ttg gag gaa cgt ata cac      480
Glu Met Glu Asp Arg Lys Ala Ala Lys Ile Leu Glu Glu Arg Ile His
145                 150                 155                 160 gag gaa ttc aag agg aaa gag gaa gaa agg cgg cga ggg gaa gaa          528
Glu Glu Phe Lys Arg Lys Glu Glu Glu Arg Arg Arg Gly Glu Glu
                165                 170                 175 cag att cgg ctc caa gag gag cag agg gca aag gaa ctc tac tgg act      576
Gln Ile Arg Leu Gln Glu Glu Gln Arg Ala Lys Glu Leu Tyr Trp Thr
            180                 185                 190 ctg aag cag gcc cag ctg cac agc caa gcc agt gag aat gag gag cgt      624
Leu Lys Gln Ala Gln Leu His Ser Gln Ala Ser Glu Asn Glu Glu Arg
        195                 200                 205 gaa tgg gaa gaa cag ctg cgg aga tcc aag gct gct gat gaa gag agg      672
Glu Trp Glu Glu Gln Leu Arg Arg Ser Lys Ala Ala Asp Glu Glu Arg
210                 215                 220 agc cgt cgt gct cag cga gcc cgg gat gag tac cgg cgc cat tca ctc      720
Ser Arg Arg Ala Gln Arg Ala Arg Asp Glu Tyr Arg Arg His Ser Leu
225                 230                 235                 240 cga gcc atc cag aag ggc act gtt gct ggc cta agc acc atg ttc caa      768
Arg Ala Ile Gln Lys Gly Thr Val Ala Gly Leu Ser Thr Met Phe Gln
                245                 250                 255 gag ctt ggc cag aac cac gag caa gag gca aga ctt tat cac caa ctt      816
Glu Leu Gly Gln Asn His Glu Gln Glu Ala Arg Leu Tyr His Gln Leu
            260                 265                 270 cct gac acc agt cca cca tca ccc ctc aca gga cct gac agg acc tgg      864
Pro Asp Thr Ser Pro Pro Ser Pro Leu Thr Gly Pro Asp Arg Thr Trp
        275                 280                 285 gag cga cct ctg cgt cca ctc tcc aga gaa gtc atc gtg cgc tgg ttc      912
Glu Arg Pro Leu Arg Pro Leu Ser Arg Glu Val Ile Val Arg Trp Phe
    290                 295                 300 aag gag gaa cag ctg cct cgc cga gca ggc ttt gag agg aac acc aag      960
Lys Glu Glu Gln Leu Pro Arg Arg Ala Gly Phe Glu Arg Asn Thr Lys
305                 310                 315                 320 tcc atc gcc cct tgg ttt cat gga att att agc cga gag agt gca gaa     1008
Ser Ile Ala Pro Trp Phe His Gly Ile Ile Ser Arg Glu Ser Ala Glu
                325                 330                 335 gac ctt ctg gag aat atg acc gag gga gca ttt ctg gtc cgg gtc agt     1056
Asp Leu Leu Glu Asn Met Thr Glu Gly Ala Phe Leu Val Arg Val Ser
            340                 345                 350 gag aag atc tgg ggt tat acc ctg tcc tac cgc ctg cag aga ggc ttc     1104
Glu Lys Ile Trp Gly Tyr Thr Leu Ser Tyr Arg Leu Gln Arg Gly Phe
        355                 360                 365 aaa cac ttc ctt gtg gat gct tct ggg gac ttc tac agc ttt ctg gga     1152
Lys His Phe Leu Val Asp Ala Ser Gly Asp Phe Tyr Ser Phe Leu Gly
    370                 375                 380 gtg gac cct aat cgc cat gcc acc cta aca gat ctc att gat ttc cac     1200
Val Asp Pro Asn Arg His Ala Thr Leu Thr Asp Leu Ile Asp Phe His
385                 390                 395                 400 aag gag gag atc atc act gtt tca ggg gga gag ttg cta cag gaa ccc     1248
Lys Glu Glu Ile Ile Thr Val Ser Gly Gly Glu Leu Leu Gln Glu Pro
                405                 410                 415 tgt gga cag agg gat agc cca cca gac tat cac ctg ttg ttt gaa tga     1296
Cys Gly Gln Arg Asp Ser Pro Pro Asp Tyr His Leu Leu Phe Glu
            420                 425                 430
```

```
<210> SEQ ID NO 2
<211> LENGTH: 431
<212> TYPE: PRT
<213> ORGANISM: Mus musculus

<400> SEQUENCE: 2

Met Leu Gln Gln Ile Leu Gln Asp Met Tyr Ile Asp Pro Glu Leu Leu
1               5                   10                  15

Ala Glu Leu Ser Asp Val Gln Lys His Ile Leu Phe Tyr Lys Met Arg
            20                  25                  30

Glu Glu Gln Leu Arg Arg Trp Arg Glu Arg Glu Ala Trp Asp Ala Leu
        35                  40                  45

Ala Gln Ala Glu Gly Leu Arg Pro Ala Lys Val Lys Arg Ala Ser Asn
    50                  55                  60

Lys His Leu Gln Trp Leu Leu Gly Ala Asp Gly Glu Val Trp Val Trp
65                  70                  75                  80

Val Met Gly Glu Gly Pro Gly Asp Lys Pro Tyr Glu Glu Ile Ser Glu
                85                  90                  95

Glu Leu Ile Ala Glu Arg Ala Arg Leu Gln Ala Gln Lys Glu Ala Glu
            100                 105                 110

Glu Leu Trp Arg Gln Lys Glu Ala Glu Ile Thr Lys Lys Phe Arg Asp
        115                 120                 125

Ala Leu Ala Asn Glu Lys Ala Arg Ile Leu Ala Glu Lys Trp Lys Val
    130                 135                 140

Glu Met Glu Asp Arg Lys Ala Ala Lys Ile Leu Glu Glu Arg Ile His
145                 150                 155                 160

Glu Glu Phe Lys Arg Lys Glu Glu Glu Arg Arg Arg Gly Glu Glu
                165                 170                 175

Gln Ile Arg Leu Gln Glu Glu Gln Arg Ala Lys Glu Leu Tyr Trp Thr
            180                 185                 190

Leu Lys Gln Ala Gln Leu His Ser Gln Ala Ser Glu Asn Glu Glu Arg
        195                 200                 205

Glu Trp Glu Glu Gln Leu Arg Arg Ser Lys Ala Ala Asp Glu Glu Arg
    210                 215                 220

Ser Arg Arg Ala Gln Arg Ala Arg Asp Glu Tyr Arg Arg His Ser Leu
225                 230                 235                 240

Arg Ala Ile Gln Lys Gly Thr Val Ala Gly Leu Ser Thr Met Phe Gln
                245                 250                 255

Glu Leu Gly Gln Asn His Glu Gln Glu Ala Arg Leu Tyr His Gln Leu
            260                 265                 270

Pro Asp Thr Ser Pro Pro Ser Pro Leu Thr Gly Pro Asp Arg Thr Trp
        275                 280                 285

Glu Arg Pro Leu Arg Pro Leu Ser Arg Glu Val Ile Val Arg Trp Phe
    290                 295                 300

Lys Glu Glu Gln Leu Pro Arg Arg Ala Gly Phe Glu Arg Asn Thr Lys
305                 310                 315                 320

Ser Ile Ala Pro Trp Phe His Gly Ile Ile Ser Arg Glu Ser Ala Glu
                325                 330                 335

Asp Leu Leu Glu Asn Met Thr Glu Gly Ala Phe Leu Val Arg Val Ser
            340                 345                 350

Glu Lys Ile Trp Gly Tyr Thr Leu Ser Tyr Arg Leu Gln Arg Gly Phe
        355                 360                 365

Lys His Phe Leu Val Asp Ala Ser Gly Asp Phe Tyr Ser Phe Leu Gly
    370                 375                 380
```

-continued

```
Val Asp Pro Asn Arg His Ala Thr Leu Thr Asp Leu Ile Asp Phe His
385                 390                 395                 400

Lys Glu Glu Ile Ile Thr Val Ser Gly Gly Glu Leu Leu Gln Glu Pro
            405                 410                 415

Cys Gly Gln Arg Asp Ser Pro Pro Asp Tyr His Leu Leu Phe Glu
        420                 425                 430

<210> SEQ ID NO 3
<211> LENGTH: 1302
<212> TYPE: DNA
<213> ORGANISM: Homo sapiens
<220> FEATURE:
<221> NAME/KEY: CDS
<222> LOCATION: (1)..(1302)

<400> SEQUENCE: 3 atg ctg cag cag atc ctg cac gac atg tac atc gac ccc gag ctc ctt      48
Met Leu Gln Gln Ile Leu His Asp Met Tyr Ile Asp Pro Glu Leu Leu
1               5                   10                  15 gcc gag ctc agc gat gtg cag aag cac atc ctc ttc tac aaa atg cgg      96
Ala Glu Leu Ser Asp Val Gln Lys His Ile Leu Phe Tyr Lys Met Arg
                20                  25                  30 gag gag cag ctg agg cgc tgg aag gag cgg gag act tgg gag gcc ctg     144
Glu Glu Gln Leu Arg Arg Trp Lys Glu Arg Glu Thr Trp Glu Ala Leu
            35                  40                  45 gcc cag gac gag ggt ctc agg cct cca aag acc aag cga gca gcg agt     192
Ala Gln Asp Glu Gly Leu Arg Pro Pro Lys Thr Lys Arg Ala Ala Ser
        50                  55                  60 gac aag cac atc caa tgg ctc cta ggg gca gat ggc gag gtc tgg gtc     240
Asp Lys His Ile Gln Trp Leu Leu Gly Ala Asp Gly Glu Val Trp Val
65                  70                  75                  80 tgg atc atg gga gaa ggc cct ggt gac aag ccc tac gaa gag atc tct     288
Trp Ile Met Gly Glu Gly Pro Gly Asp Lys Pro Tyr Glu Glu Ile Ser
                85                  90                  95 gag gag ctg att gca gag agg gcg cgg ctg cag gca cag agg gaa gct     336
Glu Glu Leu Ile Ala Glu Arg Ala Arg Leu Gln Ala Gln Arg Glu Ala
            100                 105                 110 gag gag ctc tgg aga cag aag gag gca gag atc acc aag aag ttc cgg     384
Glu Glu Leu Trp Arg Gln Lys Glu Ala Glu Ile Thr Lys Lys Phe Arg
        115                 120                 125 gat gct ctg gcc aat gag aaa gcc cgg atc ttg gcg gag aag tgg aaa     432
Asp Ala Leu Ala Asn Glu Lys Ala Arg Ile Leu Ala Glu Lys Trp Lys
    130                 135                 140 gtg gag atg gaa gac cgc aag gct gcc aaa gtc ctg gag gaa cgc atc     480
Val Glu Met Glu Asp Arg Lys Ala Ala Lys Val Leu Glu Glu Arg Ile
145                 150                 155                 160 cac gag gaa ttc aag agg aaa gag gaa gag agg aag cga gga gaa         528
His Glu Glu Phe Lys Arg Lys Glu Glu Glu Arg Lys Arg Gly Glu
                165                 170                 175 gag cag att cgc ctc cag gaa gag cag agg gcg aag gag ctc tac tgg     576
Glu Gln Ile Arg Leu Gln Glu Glu Gln Arg Ala Lys Glu Leu Tyr Trp
            180                 185                 190 acc ctg aag cag gct cag ctg cat tgc caa gcc agt gag aaa gag gag     624
Thr Leu Lys Gln Ala Gln Leu His Cys Gln Ala Ser Glu Lys Glu Glu
        195                 200                 205 cga gag tgg gaa gaa cag ctg cgg aga tcc aag gcg gct gat gag gag     672
Arg Glu Trp Glu Glu Gln Leu Arg Arg Ser Lys Ala Ala Asp Glu Glu
    210                 215                 220 agg agc cgc cga gcc cag cgc gcc cgg gac gag tac cga cac cac tcg     720
Arg Ser Arg Arg Ala Gln Arg Ala Arg Asp Glu Tyr Arg His His Ser
```

```
                    225                 230                 235                 240
ctc cgt gct atc cag aag ggc acg gtc gct ggc ctc agc tcc atg ttc        768
Leu Arg Ala Ile Gln Lys Gly Thr Val Ala Gly Leu Ser Ser Met Phe
                245                 250                 255 cgg gag ctt ggc cag agc cat gag cag gag gca aga ctc tac cac cac        816
Arg Glu Leu Gly Gln Ser His Glu Gln Glu Ala Arg Leu Tyr His His
            260                 265                 270 ctc ccc gac ccg ggt ctg ccg cag ccc ctt gcc ctg ccg gtc agc agg        864
Leu Pro Asp Pro Gly Leu Pro Gln Pro Leu Ala Leu Pro Val Ser Arg
            275                 280                 285 acc tgg gag cgc ccg ctg cgc cca gtc tcc aga gat gtc atc gtc cgc        912
Thr Trp Glu Arg Pro Leu Arg Pro Val Ser Arg Asp Val Ile Val Arg
        290                 295                 300 tgg ttt aag gag gag cag ctg cct cgc cga gct ggc ttc gag agg aac        960
Trp Phe Lys Glu Glu Gln Leu Pro Arg Arg Ala Gly Phe Glu Arg Asn
305                 310                 315                 320 acc aag ttc atc gcc ccc tgg ttc cat gga att att agc cga gaa gat        1008
Thr Lys Phe Ile Ala Pro Trp Phe His Gly Ile Ile Ser Arg Glu Asp
                325                 330                 335 gca gaa gct ctc ctg gag aac atg act gag gga gca ttc ctg gtc cgg        1056
Ala Glu Ala Leu Leu Glu Asn Met Thr Glu Gly Ala Phe Leu Val Arg
            340                 345                 350 gtc agt gag aaa atc tgg ggt tac acc ctc tcc tac cgc ctg cag aaa        1104
Val Ser Glu Lys Ile Trp Gly Tyr Thr Leu Ser Tyr Arg Leu Gln Lys
            355                 360                 365 ggg ttc aaa cac ttt ctt gtg gat gct tct ggg gat ttt tac agc ttc        1152
Gly Phe Lys His Phe Leu Val Asp Ala Ser Gly Asp Phe Tyr Ser Phe
        370                 375                 380 ctg gga gtg gac ccc aat cgc cat gca acg ctc acg gat ctc gtt gat        1200
Leu Gly Val Asp Pro Asn Arg His Ala Thr Leu Thr Asp Leu Val Asp
385                 390                 395                 400 ttc cat aag gag gaa att atc act gtt tca gga gga gag tta ctt cag        1248
Phe His Lys Glu Glu Ile Ile Thr Val Ser Gly Gly Glu Leu Leu Gln
                405                 410                 415 gaa ccc tgc gga cag agg gac agc cca cca gac tac cat ctg ttg ttt        1296
Glu Pro Cys Gly Gln Arg Asp Ser Pro Pro Asp Tyr His Leu Leu Phe
            420                 425                 430 gaa taa                                                                1302
Glu

<210> SEQ ID NO 4
<211> LENGTH: 433
<212> TYPE: PRT
<213> ORGANISM: Homo sapiens

<400> SEQUENCE: 4

Met Leu Gln Gln Ile Leu His Asp Met Tyr Ile Asp Pro Glu Leu Leu
1               5                   10                  15

Ala Glu Leu Ser Asp Val Gln Lys His Ile Leu Phe Tyr Lys Met Arg
                20                  25                  30

Glu Glu Gln Leu Arg Arg Trp Lys Glu Arg Glu Thr Trp Glu Ala Leu
            35                  40                  45

Ala Gln Asp Glu Gly Leu Arg Pro Pro Lys Thr Lys Arg Ala Ala Ser
        50                  55                  60

Asp Lys His Ile Gln Trp Leu Leu Gly Ala Asp Gly Glu Val Trp Val
65                  70                  75                  80

Trp Ile Met Gly Glu Gly Pro Gly Asp Lys Pro Tyr Glu Glu Ile Ser
                85                  90                  95
```

-continued

```
Glu Glu Leu Ile Ala Glu Arg Ala Arg Leu Gln Ala Gln Arg Glu Ala
            100                 105                 110
Glu Glu Leu Trp Arg Gln Lys Glu Ala Glu Ile Thr Lys Lys Phe Arg
        115                 120                 125
Asp Ala Leu Ala Asn Glu Lys Ala Arg Ile Leu Ala Glu Lys Trp Lys
    130                 135                 140
Val Glu Met Glu Asp Arg Lys Ala Ala Lys Val Leu Glu Glu Arg Ile
145                 150                 155                 160
His Glu Glu Phe Lys Arg Lys Glu Glu Glu Arg Lys Arg Gly Glu
                165                 170                 175
Glu Gln Ile Arg Leu Gln Glu Gln Arg Ala Lys Glu Leu Tyr Trp
            180                 185                 190
Thr Leu Lys Gln Ala Gln Leu His Cys Gln Ala Ser Glu Lys Glu Glu
        195                 200                 205
Arg Glu Trp Glu Glu Gln Leu Arg Arg Ser Lys Ala Ala Asp Glu Glu
    210                 215                 220
Arg Ser Arg Arg Ala Gln Arg Ala Arg Asp Glu Tyr Arg His His Ser
225                 230                 235                 240
Leu Arg Ala Ile Gln Lys Gly Thr Val Ala Gly Leu Ser Ser Met Phe
                245                 250                 255
Arg Glu Leu Gly Gln Ser His Glu Gln Glu Ala Arg Leu Tyr His His
            260                 265                 270
Leu Pro Asp Pro Gly Leu Pro Gln Pro Leu Ala Leu Pro Val Ser Arg
        275                 280                 285
Thr Trp Glu Arg Pro Leu Arg Pro Val Ser Arg Asp Val Ile Val Arg
    290                 295                 300
Trp Phe Lys Glu Glu Gln Leu Pro Arg Arg Ala Gly Phe Glu Arg Asn
305                 310                 315                 320
Thr Lys Phe Ile Ala Pro Trp Phe His Gly Ile Ile Ser Arg Glu Asp
                325                 330                 335
Ala Glu Ala Leu Leu Glu Asn Met Thr Glu Gly Ala Phe Leu Val Arg
            340                 345                 350
Val Ser Glu Lys Ile Trp Gly Tyr Thr Leu Ser Tyr Arg Leu Gln Lys
        355                 360                 365
Gly Phe Lys His Phe Leu Val Asp Ala Ser Gly Asp Phe Tyr Ser Phe
    370                 375                 380
Leu Gly Val Asp Pro Asn Arg His Ala Thr Leu Thr Asp Leu Val Asp
385                 390                 395                 400
Phe His Lys Glu Glu Ile Ile Thr Val Ser Gly Gly Glu Leu Leu Gln
                405                 410                 415
Glu Pro Cys Gly Gln Arg Asp Ser Pro Pro Asp Tyr His Leu Leu Phe
            420                 425                 430
Glu
```

```
<210> SEQ ID NO 5
<211> LENGTH: 1263
<212> TYPE: DNA
<213> ORGANISM: Mus musculus
<220> FEATURE:
<221> NAME/KEY: CDS
<222> LOCATION: (1)..(1263)

<400> SEQUENCE: 5 atg ctg agg cag ata ctg tca gat atg ttc ata gac cct gac ctg ctg      48
Met Leu Arg Gln Ile Leu Ser Asp Met Phe Ile Asp Pro Asp Leu Leu
1               5                   10                  15
```

```
gca gag ctc agc gaa gag cag aaa cag atc ttg ttc tac aag atg aga       96
Ala Glu Leu Ser Glu Glu Gln Lys Gln Ile Leu Phe Tyr Lys Met Arg
         20                  25                  30 gag gaa cag atc cga cga tgg aaa gaa aga gaa gcg gcc atg gaa aga      144
Glu Glu Gln Ile Arg Arg Trp Lys Glu Arg Glu Ala Ala Met Glu Arg
 35                  40                  45 aag gag tcc ttg cca gtg aaa tcc agg cca aaa aaa gag aat ggc aag      192
Lys Glu Ser Leu Pro Val Lys Ser Arg Pro Lys Lys Glu Asn Gly Lys
     50                  55                  60 tct gtc cat tgg aag ctg ggc gcc gat aag cag gtg tgg gtt tgg gta      240
Ser Val His Trp Lys Leu Gly Ala Asp Lys Gln Val Trp Val Trp Val
 65                  70                  75                  80 atg ggc gag cac cat ctg gac aaa ccc tat gat gtg ctg tgt gat gag      288
Met Gly Glu His His Leu Asp Lys Pro Tyr Asp Val Leu Cys Asp Glu
                 85                  90                  95 atc ctt gcg gag agg gag cat ctg aga gca gcg aag gat tca gag ctc      336
Ile Leu Ala Glu Arg Glu His Leu Arg Ala Ala Lys Asp Ser Glu Leu
            100                 105                 110 agg aaa act cag tct cta gaa ctc gcc aat agc tta aaa ata aag tca      384
Arg Lys Thr Gln Ser Leu Glu Leu Ala Asn Ser Leu Lys Ile Lys Ser
        115                 120                 125 cag aac tgt gat ctg caa gca atg aag aag aca gag cct cag aat gtc      432
Gln Asn Cys Asp Leu Gln Ala Met Lys Lys Thr Glu Pro Gln Asn Val
130                 135                 140 acc agg aaa gca gct tca gaa gag gca tca ggt caa gga ccc aga gca      480
Thr Arg Lys Ala Ala Ser Glu Glu Ala Ser Gly Gln Gly Pro Arg Ala
145                 150                 155                 160 ata cca acc agg aag gat gac aaa gcc caa act aaa ccc gtc aag gaa      528
Ile Pro Thr Arg Lys Asp Asp Lys Ala Gln Thr Lys Pro Val Lys Glu
                165                 170                 175 aaa gac cac gag gaa atg aag cag aca gag gat gag aaa acc aag cag      576
Lys Asp His Glu Glu Met Lys Gln Thr Glu Asp Glu Lys Thr Lys Gln
            180                 185                 190 ata tac aag agc tgg aaa gaa gac tca gaa tgg caa gca tct ctg cga      624
Ile Tyr Lys Ser Trp Lys Glu Asp Ser Glu Trp Gln Ala Ser Leu Arg
        195                 200                 205 aaa tct aag gcg gct gat gag aag aga cgc tct tta gct aaa caa gca      672
Lys Ser Lys Ala Ala Asp Glu Lys Arg Arg Ser Leu Ala Lys Gln Ala
210                 215                 220 cgg gaa gac tac aag agg cta tcc caa agg ggg agg agt ggg gac gga      720
Arg Glu Asp Tyr Lys Arg Leu Ser Gln Arg Gly Arg Ser Gly Asp Gly
225                 230                 235                 240 ctg cag aac cca ctg aca ggt cca cag aag ccc aga aga cct cct ctt      768
Leu Gln Asn Pro Leu Thr Gly Pro Gln Lys Pro Arg Arg Pro Pro Leu
                245                 250                 255 cct ccg aag ccc cag ttc cta cag ccg ctg gga atc cct cca aag tct      816
Pro Pro Lys Pro Gln Phe Leu Gln Pro Leu Gly Ile Pro Pro Lys Ser
            260                 265                 270 tta ggg aat cag ggg gtg ata agg acc gag atc agc tcc gcc cag atg      864
Leu Gly Asn Gln Gly Val Ile Arg Thr Glu Ile Ser Ser Ala Gln Met
        275                 280                 285 gac acc att cga tgg ttc aaa gag gaa cag ttg cca ttc cgt gca ggt      912
Asp Thr Ile Arg Trp Phe Lys Glu Glu Gln Leu Pro Phe Arg Ala Gly
290                 295                 300 tac cag aaa aac tca gac acc att gct cct tgg ttc cat ggg att ctc      960
Tyr Gln Lys Asn Ser Asp Thr Ile Ala Pro Trp Phe His Gly Ile Leu
305                 310                 315                 320 aca ctg aag aaa gca aat gaa ctt ctg agc aca ggt gtg ccg gga agt     1008
Thr Leu Lys Lys Ala Asn Glu Leu Leu Ser Thr Gly Val Pro Gly Ser
```

```
                         325                 330                 335
ttt ttg att cga gtc agt gaa aag atc aag ggc tat gcc ctg tcc tac   1056
Phe Leu Ile Arg Val Ser Glu Lys Ile Lys Gly Tyr Ala Leu Ser Tyr
            340                 345                 350 ctg tct gag gaa ggc tgc aaa cat ttc ctt ata gat gca tct gcc aac   1104
Leu Ser Glu Glu Gly Cys Lys His Phe Leu Ile Asp Ala Ser Ala Asn
                355                 360                 365 tct tac agc ttc ctg ggt gtg gac cag ctg cag cat gct aca ctg gca   1152
Ser Tyr Ser Phe Leu Gly Val Asp Gln Leu Gln His Ala Thr Leu Ala
        370                 375                 380 gat ttg gtg gaa tat cac aag gag gag ccc ata acc tct ctg ggg aag   1200
Asp Leu Val Glu Tyr His Lys Glu Glu Pro Ile Thr Ser Leu Gly Lys
385                 390                 395                 400 gaa ctc ctt ctg tac ccc tgt ggt caa caa gac aag ctg ccc gac tac   1248
Glu Leu Leu Leu Tyr Pro Cys Gly Gln Gln Asp Lys Leu Pro Asp Tyr
                405                 410                 415 ctg gag ctc ttc cag                                               1263
Leu Glu Leu Phe Gln
            420

<210> SEQ ID NO 6
<211> LENGTH: 421
<212> TYPE: PRT
<213> ORGANISM: Mus musculus

<400> SEQUENCE: 6

Met Leu Arg Gln Ile Leu Ser Asp Met Phe Ile Asp Pro Asp Leu Leu
1               5                   10                  15

Ala Glu Leu Ser Glu Glu Gln Lys Gln Ile Leu Phe Tyr Lys Met Arg
            20                  25                  30

Glu Glu Gln Ile Arg Arg Trp Lys Glu Arg Glu Ala Ala Met Glu Arg
        35                  40                  45

Lys Glu Ser Leu Pro Val Lys Ser Arg Pro Lys Lys Glu Asn Gly Lys
    50                  55                  60

Ser Val His Trp Lys Leu Gly Ala Asp Lys Gln Val Trp Val Trp Val
65                  70                  75                  80

Met Gly Glu His His Leu Asp Lys Pro Tyr Asp Val Leu Cys Asp Glu
                85                  90                  95

Ile Leu Ala Glu Arg Glu His Leu Arg Ala Ala Lys Asp Ser Glu Leu
            100                 105                 110

Arg Lys Thr Gln Ser Leu Glu Leu Ala Asn Ser Leu Lys Ile Lys Ser
        115                 120                 125

Gln Asn Cys Asp Leu Gln Ala Met Lys Lys Thr Glu Pro Gln Asn Val
    130                 135                 140

Thr Arg Lys Ala Ala Ser Glu Glu Ala Ser Gly Gln Gly Pro Arg Ala
145                 150                 155                 160

Ile Pro Thr Arg Lys Asp Asp Lys Ala Gln Thr Lys Pro Val Lys Glu
                165                 170                 175

Lys Asp His Glu Glu Met Lys Gln Thr Glu Asp Glu Lys Thr Lys Gln
            180                 185                 190

Ile Tyr Lys Ser Trp Lys Glu Asp Ser Glu Trp Gln Ala Ser Leu Arg
        195                 200                 205

Lys Ser Lys Ala Ala Asp Glu Lys Arg Arg Ser Leu Ala Lys Gln Ala
    210                 215                 220

Arg Glu Asp Tyr Lys Arg Leu Ser Gln Arg Gly Arg Ser Gly Asp Gly
225                 230                 235                 240
```

```
Leu Gln Asn Pro Leu Thr Gly Pro Gln Lys Pro Arg Arg Pro Pro Leu
            245                 250                 255

Pro Pro Lys Pro Gln Phe Leu Gln Pro Leu Gly Ile Pro Pro Lys Ser
        260                 265                 270

Leu Gly Asn Gln Gly Val Ile Arg Thr Glu Ile Ser Ser Ala Gln Met
            275                 280                 285

Asp Thr Ile Arg Trp Phe Lys Glu Glu Gln Leu Pro Phe Arg Ala Gly
        290                 295                 300

Tyr Gln Lys Asn Ser Asp Thr Ile Ala Pro Trp Phe His Gly Ile Leu
305                 310                 315                 320

Thr Leu Lys Lys Ala Asn Glu Leu Leu Ser Thr Gly Val Pro Gly Ser
                325                 330                 335

Phe Leu Ile Arg Val Ser Glu Lys Ile Lys Gly Tyr Ala Leu Ser Tyr
            340                 345                 350

Leu Ser Glu Glu Gly Cys Lys His Phe Leu Ile Asp Ala Ser Ala Asn
            355                 360                 365

Ser Tyr Ser Phe Leu Gly Val Asp Gln Leu Gln His Ala Thr Leu Ala
    370                 375                 380

Asp Leu Val Glu Tyr His Lys Glu Glu Pro Ile Thr Ser Leu Gly Lys
385                 390                 395                 400

Glu Leu Leu Leu Tyr Pro Cys Gly Gln Gln Asp Lys Leu Pro Asp Tyr
                405                 410                 415

Leu Glu Leu Phe Gln
            420

<210> SEQ ID NO 7
<211> LENGTH: 1365
<212> TYPE: DNA
<213> ORGANISM: Homo sapiens
<220> FEATURE:
<221> NAME/KEY: CDS
<222> LOCATION: (1)..(1365)

<400> SEQUENCE: 7 atg ctg aaa cag ata ctg tcg gag atg tac ata gat cct gat cta ctg    48
Met Leu Lys Gln Ile Leu Ser Glu Met Tyr Ile Asp Pro Asp Leu Leu
1               5                   10                  15 gca gag ctc agc gaa gaa cag aaa cag atc ctg ttc ttc aag atg aga    96
Ala Glu Leu Ser Glu Glu Gln Lys Gln Ile Leu Phe Phe Lys Met Arg
            20                  25                  30 gag gaa cag atc cga cga tgg aaa gaa aga gaa gca gct atg gaa aga   144
Glu Glu Gln Ile Arg Arg Trp Lys Glu Arg Glu Ala Ala Met Glu Arg
        35                  40                  45 aag gag tcc ctg cca gtg aaa ccc aga cca aag aaa gag aat ggc aaa   192
Lys Glu Ser Leu Pro Val Lys Pro Arg Pro Lys Lys Glu Asn Gly Lys
    50                  55                  60 tcg gtt cat tgg aaa ctt gga gct gat aag gaa gtc tgg gta tgg gtg   240
Ser Val His Trp Lys Leu Gly Ala Asp Lys Glu Val Trp Val Trp Val
65                  70                  75                  80 atg ggc gaa cac cat cta gat aaa ccc tat gat gtg ctc tgt aat gaa   288
Met Gly Glu His His Leu Asp Lys Pro Tyr Asp Val Leu Cys Asn Glu
                85                  90                  95 att att gct gag agg gcc cgg ctg aaa gca gaa cag gag gca gaa gag   336
Ile Ile Ala Glu Arg Ala Arg Leu Lys Ala Glu Gln Glu Ala Glu Glu
            100                 105                 110 ccc aga aaa act cac tct gaa gaa ttc acc aat agc ttg aaa aca aaa   384
Pro Arg Lys Thr His Ser Glu Glu Phe Thr Asn Ser Leu Lys Thr Lys
        115                 120                 125
```

-continued

| | |
|---|---|
| tca cag tac cat gat ctg cag gct ccg gat aac cag cag act aaa gac<br>Ser Gln Tyr His Asp Leu Gln Ala Pro Asp Asn Gln Gln Thr Lys Asp<br>130                               135                        140 | 432 |
| atc tgg aag aaa gtg gca gaa aag gag gaa ctg gag caa gga tct agg<br>Ile Trp Lys Lys Val Ala Glu Lys Glu Glu Leu Glu Gln Gly Ser Arg<br>145                         150                        155                     160 | 480 |
| cca gca cca acc ctg gaa gaa gag aaa atc cga tca ctc tcc agt tct<br>Pro Ala Pro Thr Leu Glu Glu Glu Lys Ile Arg Ser Leu Ser Ser Ser<br>                     165                        170                     175 | 528 |
| tca aga aat att caa caa atg ttg gca gat tca atc aat cgt atg aag<br>Ser Arg Asn Ile Gln Gln Met Leu Ala Asp Ser Ile Asn Arg Met Lys<br>     180                        185                        190 | 576 |
| gca tat gca ttt cac cag aag aaa gaa tct atg aag aaa aaa caa gat<br>Ala Tyr Ala Phe His Gln Lys Lys Glu Ser Met Lys Lys Lys Gln Asp<br>                195                        200                     205 | 624 |
| gaa gaa ata aat caa ata gaa gaa gag aga acg aag cag att tgt aag<br>Glu Glu Ile Asn Gln Ile Glu Glu Glu Arg Thr Lys Gln Ile Cys Lys<br>210                               215                        220 | 672 |
| agc tgg aaa gaa gac tcg gaa tgg cag gca tct ctg cga aaa tcc aaa<br>Ser Trp Lys Glu Asp Ser Glu Trp Gln Ala Ser Leu Arg Lys Ser Lys<br>225                               230                        235                     240 | 720 |
| gca gct gat gag aag aga cgc tcc ttg gct aaa caa gca cga gaa gac<br>Ala Ala Asp Glu Lys Arg Arg Ser Leu Ala Lys Gln Ala Arg Glu Asp<br>                             245                        250                     255 | 768 |
| tac aag agg ttg tcc ctc ggg gcc cag aaa gga aga ggc ggt gag agg<br>Tyr Lys Arg Leu Ser Leu Gly Ala Gln Lys Gly Arg Gly Gly Glu Arg<br>               260                        265                        270 | 816 |
| ctg caa agc ccc ttg cgt gtt ccg cag aaa cca gaa aga cct ccc ctt<br>Leu Gln Ser Pro Leu Arg Val Pro Gln Lys Pro Glu Arg Pro Pro Leu<br>                     275                        280                     285 | 864 |
| cca ccc aag cct cag ttc cta aac tca ggg gca tat cct caa aaa cct<br>Pro Pro Lys Pro Gln Phe Leu Asn Ser Gly Ala Tyr Pro Gln Lys Pro<br>290                               295                        300 | 912 |
| ctt aga aat cag gga gtg gtg agg aca ctg tcc agc tct gcc caa gag<br>Leu Arg Asn Gln Gly Val Val Arg Thr Leu Ser Ser Ser Ala Gln Glu<br>305                               310                        315                     320 | 960 |
| gac atc atc cgg tgg ttt aaa gag gag cag cta cca ctt cga gcg ggc<br>Asp Ile Ile Arg Trp Phe Lys Glu Glu Gln Leu Pro Leu Arg Ala Gly<br>                           325                        330                     335 | 1008 |
| tac cag aaa acc tca gac acc ata gcc ccc tgg ttc cat gga att ctc<br>Tyr Gln Lys Thr Ser Asp Thr Ile Ala Pro Trp Phe His Gly Ile Leu<br>                     340                        345                     350 | 1056 |
| aca ctc aag aaa gca aat gaa ctt ctt ctg agc aca ggc atg ccc ggc<br>Thr Leu Lys Lys Ala Asn Glu Leu Leu Leu Ser Thr Gly Met Pro Gly<br>               355                        360                        365 | 1104 |
| agt ttt ctc atc cga gtc agt gaa agg atc aaa ggc tat gcc ctg tcc<br>Ser Phe Leu Ile Arg Val Ser Glu Arg Ile Lys Gly Tyr Ala Leu Ser<br>370                               375                        380 | 1152 |
| tat ctg tcg gag gac ggc tgt aaa cat ttc ctc atc gat gcc tct gca<br>Tyr Leu Ser Glu Asp Gly Cys Lys His Phe Leu Ile Asp Ala Ser Ala<br>385                               390                        395                     400 | 1200 |
| gac gcc tac agc ttc ctg ggc gtg gac cag cta cag cat gcc acc ttg<br>Asp Ala Tyr Ser Phe Leu Gly Val Asp Gln Leu Gln His Ala Thr Leu<br>                           405                        410                     415 | 1248 |
| gcg gat ttg gtg gaa tat cac aag gag gaa ccc atc act tcc ctg ggg<br>Ala Asp Leu Val Glu Tyr His Lys Glu Glu Pro Ile Thr Ser Leu Gly<br>                     420                        425                     430 | 1296 |
| aag gag ctc ctt ctc tat ccc tgt ggt cag cag gac cag ctg cct gac<br>Lys Glu Leu Leu Leu Tyr Pro Cys Gly Gln Gln Asp Gln Leu Pro Asp<br>                     435                        440                     445 | 1344 |

```
tac ctg gag ctg ttt gag tga                                    1365
Tyr Leu Glu Leu Phe Glu
    450
```

<210> SEQ ID NO 8
<211> LENGTH: 454
<212> TYPE: PRT
<213> ORGANISM: Homo sapiens

<400> SEQUENCE: 8

```
Met Leu Lys Gln Ile Leu Ser Glu Met Tyr Ile Asp Pro Asp Leu Leu
1               5                  10                  15

Ala Glu Leu Ser Glu Glu Lys Gln Ile Leu Phe Phe Lys Met Arg
            20                  25                  30

Glu Glu Gln Ile Arg Arg Trp Lys Glu Arg Ala Ala Met Glu Arg
        35                  40                  45

Lys Glu Ser Leu Pro Val Lys Pro Arg Pro Lys Glu Asn Gly Lys
    50                  55                  60

Ser Val His Trp Lys Leu Gly Ala Asp Lys Glu Val Trp Val Trp Val
65                  70                  75                  80

Met Gly Glu His His Leu Asp Lys Pro Tyr Asp Val Leu Cys Asn Glu
                85                  90                  95

Ile Ile Ala Glu Arg Ala Arg Leu Lys Ala Glu Gln Glu Ala Glu Glu
            100                 105                 110

Pro Arg Lys Thr His Ser Glu Glu Phe Thr Asn Ser Leu Lys Thr Lys
        115                 120                 125

Ser Gln Tyr His Asp Leu Gln Ala Pro Asp Asn Gln Gln Thr Lys Asp
    130                 135                 140

Ile Trp Lys Lys Val Ala Glu Lys Glu Glu Leu Glu Gln Gly Ser Arg
145                 150                 155                 160

Pro Ala Pro Thr Leu Glu Glu Glu Lys Ile Arg Ser Leu Ser Ser Ser
                165                 170                 175

Ser Arg Asn Ile Gln Gln Met Leu Ala Asp Ser Ile Asn Arg Met Lys
            180                 185                 190

Ala Tyr Ala Phe His Gln Lys Lys Glu Ser Met Lys Lys Lys Gln Asp
        195                 200                 205

Glu Glu Ile Asn Gln Ile Glu Glu Glu Arg Thr Lys Gln Ile Cys Lys
    210                 215                 220

Ser Trp Lys Glu Asp Ser Glu Trp Gln Ala Ser Leu Arg Lys Ser Lys
225                 230                 235                 240

Ala Ala Asp Glu Lys Arg Arg Ser Leu Ala Lys Gln Ala Arg Glu Asp
                245                 250                 255

Tyr Lys Arg Leu Ser Leu Gly Ala Gln Lys Gly Arg Gly Glu Arg
            260                 265                 270

Leu Gln Ser Pro Leu Arg Val Pro Gln Lys Pro Glu Arg Pro Pro Leu
        275                 280                 285

Pro Pro Lys Pro Gln Phe Leu Asn Ser Gly Ala Tyr Pro Gln Lys Pro
    290                 295                 300

Leu Arg Asn Gln Gly Val Val Arg Thr Leu Ser Ser Ser Ala Gln Glu
305                 310                 315                 320

Asp Ile Ile Arg Trp Phe Lys Glu Glu Gln Leu Pro Leu Arg Ala Gly
                325                 330                 335

Tyr Gln Lys Thr Ser Asp Thr Ile Ala Pro Trp Phe His Gly Ile Leu
            340                 345                 350
```

```
Thr Leu Lys Lys Ala Asn Glu Leu Leu Ser Thr Gly Met Pro Gly
        355                 360                 365

Ser Phe Leu Ile Arg Val Ser Glu Arg Ile Lys Gly Tyr Ala Leu Ser
    370                 375                 380

Tyr Leu Ser Glu Asp Gly Cys Lys His Phe Leu Ile Asp Ala Ser Ala
385                 390                 395                 400

Asp Ala Tyr Ser Phe Leu Gly Val Asp Gln Leu Gln His Ala Thr Leu
            405                 410                 415

Ala Asp Leu Val Glu Tyr His Lys Glu Glu Pro Ile Thr Ser Leu Gly
        420                 425                 430

Lys Glu Leu Leu Leu Tyr Pro Cys Gly Gln Gln Asp Gln Leu Pro Asp
        435                 440                 445

Tyr Leu Glu Leu Phe Glu
    450
```

<210> SEQ ID NO 9
<211> LENGTH: 180
<212> TYPE: PRT
<213> ORGANISM: Homo sapiens

<400> SEQUENCE: 9

```
Met Leu Gln Gln Ile Leu His Asp Met Tyr Ile Asp Pro Glu Leu Leu
1               5                   10                  15

Ala Glu Leu Ser Asp Val Gln Lys His Ile Leu Phe Tyr Lys Met Arg
            20                  25                  30

Glu Glu Gln Leu Arg Arg Trp Lys Glu Arg Glu Thr Trp Glu Ala Leu
        35                  40                  45

Ala Gln Asp Glu Gly Leu Arg Pro Pro Lys Thr Lys Arg Ala Ala Ser
    50                  55                  60

Asp Lys His Ile Gln Trp Leu Leu Gly Ala Asp Gly Glu Val Trp Val
65                  70                  75                  80

Trp Ile Met Gly Glu Gly Pro Gly Asp Lys Pro Tyr Glu Glu Ile Ser
                85                  90                  95

Glu Glu Leu Ile Ala Glu Arg Ala Arg Leu Gln Ala Gln Arg Glu Ala
            100                 105                 110

Glu Glu Leu Trp Arg Gln Lys Glu Ala Glu Ile Thr Lys Lys Phe Arg
        115                 120                 125

Asp Ala Leu Ala Asn Glu Lys Ala Arg Ile Leu Ala Glu Lys Trp Lys
    130                 135                 140

Val Glu Met Glu Asp Arg Lys Ala Ala Lys Val Leu Glu Glu Arg Ile
145                 150                 155                 160

His Glu Glu Phe Lys Arg Lys Glu Glu Glu Arg Lys Arg Gly Glu
                165                 170                 175

Glu Gln Ile Arg
            180
```

<210> SEQ ID NO 10
<211> LENGTH: 179
<212> TYPE: PRT
<213> ORGANISM: Mus musculus

<400> SEQUENCE: 10

```
Met Leu Gln Gln Ile Leu Gln Asp Met Tyr Ile Asp Pro Glu Leu Leu
1               5                   10                  15

Ala Glu Leu Ser Asp Val Gln Lys His Ile Leu Phe Tyr Lys Met Arg
            20                  25                  30
```

```
Glu Glu Gln Leu Arg Arg Trp Arg Glu Arg Glu Ala Trp Asp Ala Leu
            35                  40                  45

Ala Gln Ala Glu Gly Leu Arg Pro Ala Lys Val Lys Arg Ala Ser Asn
 50                  55                  60

Lys His Leu Gln Trp Leu Leu Gly Ala Asp Gly Glu Val Trp Val Trp
 65                  70                  75                  80

Val Met Gly Glu Gly Pro Gly Asp Lys Pro Tyr Glu Glu Ile Ser Glu
                 85                  90                  95

Glu Leu Ile Ala Glu Arg Ala Arg Leu Gln Ala Gln Lys Glu Ala Glu
             100                 105                 110

Glu Leu Trp Arg Gln Lys Glu Ala Glu Ile Thr Lys Lys Phe Arg Asp
             115                 120                 125

Ala Leu Ala Asn Glu Lys Ala Arg Ile Leu Ala Glu Lys Trp Lys Val
 130                 135                 140

Glu Met Glu Asp Arg Lys Ala Ala Lys Ile Leu Glu Glu Arg Ile His
145                 150                 155                 160

Glu Glu Phe Lys Arg Lys Glu Glu Glu Arg Arg Arg Gly Glu Glu
                165                 170                 175

Gln Ile Arg
```

<210> SEQ ID NO 11
<211> LENGTH: 178
<212> TYPE: PRT
<213> ORGANISM: Homo sapiens

<400> SEQUENCE: 11

```
Met Leu Lys Gln Ile Leu Ser Glu Met Tyr Ile Asp Pro Asp Leu Leu
 1               5                  10                  15

Ala Glu Leu Ser Glu Glu Gln Lys Gln Ile Leu Phe Phe Lys Met Arg
                 20                  25                  30

Glu Glu Gln Ile Arg Arg Trp Lys Glu Arg Glu Ala Ala Met Glu Arg
            35                  40                  45

Lys Glu Ser Leu Pro Val Lys Pro Arg Pro Lys Lys Glu Asn Gly Lys
 50                  55                  60

Ser Val His Trp Lys Leu Gly Ala Asp Lys Glu Val Trp Val Trp Val
 65                  70                  75                  80

Met Gly Glu His His Leu Asp Lys Pro Tyr Asp Val Leu Cys Asn Glu
                 85                  90                  95

Ile Ile Ala Glu Arg Ala Arg Leu Lys Ala Glu Gln Glu Ala Glu Glu
             100                 105                 110

Pro Arg Lys Thr His Ser Glu Glu Phe Thr Asn Ser Leu Lys Thr Lys
             115                 120                 125

Ser Gln Tyr His Asp Leu Gln Ala Pro Asp Asn Gln Gln Thr Lys Asp
 130                 135                 140

Ile Trp Lys Lys Val Ala Glu Lys Glu Leu Glu Gln Gly Ser Arg
145                 150                 155                 160

Pro Ala Pro Thr Leu Glu Glu Glu Lys Ile Arg Ser Leu Ser Ser Ser
                165                 170                 175

Ser Arg
```

<210> SEQ ID NO 12
<211> LENGTH: 173
<212> TYPE: PRT
<213> ORGANISM: Mus musculus

<400> SEQUENCE: 12

Met Leu Arg Gln Ile Leu Ser Asp Met Phe Ile Asp Pro Asp Leu Leu
1               5                   10                  15

Ala Glu Leu Ser Glu Glu Gln Lys Gln Ile Leu Phe Tyr Lys Met Arg
            20                  25                  30

Glu Glu Gln Ile Arg Arg Trp Lys Glu Arg Glu Ala Ala Met Glu Arg
        35                  40                  45

Lys Glu Ser Leu Pro Val Lys Ser Arg Pro Lys Lys Glu Asn Gly Lys
    50                  55                  60

Ser Val His Trp Lys Leu Gly Ala Asp Lys Gln Val Trp Val Trp Val
65                  70                  75                  80

Met Gly Glu His His Leu Asp Lys Pro Tyr Asp Val Leu Cys Asp Glu
                85                  90                  95

Ile Leu Ala Glu Arg Glu His Leu Arg Ala Ala Lys Asp Ser Glu Leu
            100                 105                 110

Arg Lys Thr Gln Ser Leu Glu Leu Ala Asn Ser Leu Lys Ile Lys Ser
        115                 120                 125

Gln Asn Cys Asp Leu Gln Ala Met Lys Lys Thr Glu Pro Gln Asn Val
    130                 135                 140

Thr Arg Lys Ala Ala Ser Glu Glu Ala Ser Gly Gln Gly Pro Arg Ala
145                 150                 155                 160

Ile Pro Thr Arg Lys Asp Asp Lys Ala Gln Thr Lys Pro
                165                 170

<210> SEQ ID NO 13
<211> LENGTH: 93
<212> TYPE: PRT
<213> ORGANISM: Danio rerio

<400> SEQUENCE: 13

Met Leu Gln Gln Ile Leu Lys Asp Met Tyr Ile Asp Pro Asp Val Leu
1               5                   10                  15

Glu Ala Leu Asn Asp Glu Gln Lys Lys Met Leu Phe Leu Lys Met Arg
            20                  25                  30

Glu Glu His Val Arg Arg Trp Lys Glu Arg Glu Lys Leu Glu Arg
        35                  40                  45

Glu Pro Leu Lys Pro Lys Ala Lys Thr Ala His Ser Lys Ser Val Ser
    50                  55                  60

Trp Leu Leu Gly Arg Asp Gly Asp Val Gln Val Ile Val Ile Gly Glu
65                  70                  75                  80

Met Asp Glu Phe Lys Ser Ser Lys Ile Ile Tyr Ser Gly
                85                  90

<210> SEQ ID NO 14
<211> LENGTH: 139
<212> TYPE: PRT
<213> ORGANISM: Danio rerio
<220> FEATURE:
<221> NAME/KEY: UNSURE
<222> LOCATION: 128
<223> OTHER INFORMATION: Xaa is unknown

<400> SEQUENCE: 14

Met Leu Gln Gln Ile Leu Ala Asp Met Tyr Ile Asp Pro Asp Val Leu
1               5                   10                  15

Glu Ala Leu Asn Glu Glu Gln Lys Lys Ile Leu Phe Phe Lys Met Arg
            20                  25                  30

Glu Glu Gln Val Arg Arg Trp Lys Glu Arg Glu Glu Gln Glu Ser Lys

```
                35                  40                  45
Gly Glu Ile Lys Lys Glu Lys Leu Arg Lys Lys Gly Pro Cys Lys
         50                  55                  60
Asn Val Ser Trp Leu Leu Gly Arg Asp Gly Asp Val His Val Cys Ile
 65                  70                  75                  80
Ile Gly Glu Ser Asp Val Leu Glu Ser Pro Lys Leu Ile Leu Ser Glu
                 85                  90                  95
Leu Arg Asn Asn Thr Thr Ala Asn Gly Asn Asn Ile Asn Arg Ala Asn
                100                 105                 110
Ala Glu Ser Ile Lys Ser Ser Ile Lys Leu Asn Arg Val Gln Xaa
            115                 120                 125
Thr Ser Thr Glu Pro Gly Ile Gln Leu Leu Leu
        130                 135

<210> SEQ ID NO 15
<211> LENGTH: 107
<212> TYPE: PRT
<213> ORGANISM: Homo sapiens

<400> SEQUENCE: 15

Trp Phe His Gly Ile Ile Ser Arg Glu Asp Ala Glu Ala Leu Leu Glu
 1               5                  10                  15
Asn Met Thr Glu Gly Ala Phe Leu Val Arg Val Ser Glu Lys Ile Trp
                20                  25                  30
Gly Tyr Thr Leu Ser Tyr Arg Leu Gln Lys Gly Phe Lys His Phe Leu
             35                  40                  45
Val Asp Ala Ser Gly Asp Phe Tyr Ser Phe Leu Gly Val Asp Pro Asn
         50                  55                  60
Arg His Ala Thr Leu Thr Asp Leu Val Asp Phe His Lys Glu Glu Ile
 65                  70                  75                  80
Ile Thr Val Ser Gly Gly Glu Leu Leu Gln Glu Pro Cys Gly Gln Arg
                 85                  90                  95
Asp Ser Pro Pro Asp Tyr His Leu Leu Phe Glu
            100                 105

<210> SEQ ID NO 16
<211> LENGTH: 107
<212> TYPE: PRT
<213> ORGANISM: Mus musculus

<400> SEQUENCE: 16

Trp Phe His Gly Ile Ile Ser Arg Glu Ser Ala Glu Asp Leu Leu Glu
 1               5                  10                  15
Asn Met Thr Glu Gly Ala Phe Leu Val Arg Val Ser Glu Lys Ile Trp
                20                  25                  30
Gly Tyr Thr Leu Ser Tyr Arg Leu Gln Arg Gly Phe Lys His Phe Leu
             35                  40                  45
Val Asp Ala Ser Gly Asp Phe Tyr Ser Phe Leu Gly Val Asp Pro Asn
         50                  55                  60
Arg His Ala Thr Leu Thr Asp Leu Ile Asp Phe His Lys Glu Glu Ile
 65                  70                  75                  80
Ile Thr Val Ser Gly Gly Glu Leu Leu Gln Glu Pro Cys Gly Gln Arg
                 85                  90                  95
Asp Ser Pro Pro Asp Tyr His Leu Leu Phe Glu
            100                 105
```

<210> SEQ ID NO 17
<211> LENGTH: 108
<212> TYPE: PRT
<213> ORGANISM: Homo sapiens

<400> SEQUENCE: 17

Trp Phe His Gly Ile Leu Thr Leu Lys Lys Ala Asn Glu Leu Leu Leu
1               5                   10                  15

Ser Thr Gly Met Pro Gly Ser Phe Leu Ile Arg Val Ser Glu Arg Ile
            20                  25                  30

Lys Gly Tyr Ala Leu Ser Tyr Leu Ser Glu Asp Gly Cys Lys His Phe
        35                  40                  45

Leu Ile Asp Ala Ser Ala Asp Ala Tyr Ser Phe Leu Gly Val Asp Gln
    50                  55                  60

Leu Gln His Ala Thr Leu Ala Asp Leu Val Glu Tyr His Lys Glu Glu
65                  70                  75                  80

Pro Ile Thr Ser Leu Gly Lys Glu Leu Leu Tyr Pro Cys Gly Gln
                85                  90                  95

Gln Asp Gln Leu Pro Asp Tyr Leu Glu Leu Phe Glu
            100                 105

<210> SEQ ID NO 18
<211> LENGTH: 107
<212> TYPE: PRT
<213> ORGANISM: Mus musculus

<400> SEQUENCE: 18

Trp Phe His Gly Ile Leu Thr Leu Lys Lys Ala Asn Glu Leu Leu Ser
1               5                   10                  15

Thr Gly Val Pro Gly Ser Phe Leu Ile Arg Val Ser Glu Lys Ile Lys
            20                  25                  30

Gly Tyr Ala Leu Ser Tyr Leu Ser Glu Glu Gly Cys Lys His Phe Leu
        35                  40                  45

Ile Asp Ala Ser Ala Asn Ser Tyr Ser Phe Leu Gly Val Asp Gln Leu
    50                  55                  60

Gln His Ala Thr Leu Ala Asp Leu Val Glu Tyr His Lys Glu Glu Pro
65                  70                  75                  80

Ile Thr Ser Leu Gly Lys Glu Leu Leu Leu Tyr Pro Cys Gly Gln Gln
                85                  90                  95

Asp Lys Leu Pro Asp Tyr Leu Glu Leu Phe Gln
            100                 105

<210> SEQ ID NO 19
<211> LENGTH: 24
<212> TYPE: PRT
<213> ORGANISM: Mus musculus

<400> SEQUENCE: 19

Cys Leu Pro Asp Thr Ser Pro Ser Pro Leu Thr Gly Pro Asp Arg
1               5                   10                  15

Thr Trp Glu Arg Pro Leu Arg Cys
            20

<210> SEQ ID NO 20
<211> LENGTH: 17
<212> TYPE: PRT
<213> ORGANISM: Mus musculus

<400> SEQUENCE: 20

```
Cys Gly Glu Gly Pro Gly Asp Lys Pro Tyr Glu Glu Ile Ser Glu Glu
1               5                   10                  15

Cys
```

<210> SEQ ID NO 21
<211> LENGTH: 19
<212> TYPE: PRT
<213> ORGANISM: Mus musculus

<400> SEQUENCE: 21

```
Ala Asp Glu Glu Arg Ser Arg Arg Ala Gln Arg Ala Arg Asp Glu Tyr
1               5                   10                  15

Arg Arg Cys
```

<210> SEQ ID NO 22
<211> LENGTH: 19
<212> TYPE: PRT
<213> ORGANISM: Mus musculus

<400> SEQUENCE: 22

```
Cys Gly Leu Arg Pro Pro Lys Thr Lys Arg Ala Ala Ser Asp Lys His
1               5                   10                  15

Ile Gln Cys
```

<210> SEQ ID NO 23
<211> LENGTH: 18
<212> TYPE: PRT
<213> ORGANISM: Mus musculus

<400> SEQUENCE: 23

```
Asp Ala Ser Gly Asp Phe Tyr Ser Phe Leu Gly Val Asp Pro Asn Arg
1               5                   10                  15

His Cys
```

<210> SEQ ID NO 24
<211> LENGTH: 13
<212> TYPE: PRT
<213> ORGANISM: Mus musculus

<400> SEQUENCE: 24

```
Gln Gln Met Leu Ala Asp Ser Ile Asn Arg Met Lys Cys
1               5                   10
```

<210> SEQ ID NO 25
<211> LENGTH: 20
<212> TYPE: DNA
<213> ORGANISM: Artificial sequence
<220> FEATURE:
<221> NAME/KEY: misc_feature
<223> OTHER INFORMATION: Description of Artificial Sequence: Primer

<400> SEQUENCE: 25
tgctgcagca gatcctgcac                                        20

<210> SEQ ID NO 26
<211> LENGTH: 19
<212> TYPE: DNA
<213> ORGANISM: Artificial sequence
<220> FEATURE:
<221> NAME/KEY: misc_feature
<223> OTHER INFORMATION: Description of Artificial Sequence: Primer

<400> SEQUENCE: 26
cctgaagtaa ctctcctcc                                                19

<210> SEQ ID NO 27
<211> LENGTH: 21
<212> TYPE: DNA
<213> ORGANISM: Artificial sequence
<220> FEATURE:
<221> NAME/KEY: misc_feature
<223> OTHER INFORMATION: Description of Artificial Sequence: Primer

<400> SEQUENCE: 27
ccctggtgac aagccctacg a                                             21

<210> SEQ ID NO 28
<211> LENGTH: 22
<212> TYPE: DNA
<213> ORGANISM: Artificial sequence
<220> FEATURE:
<221> NAME/KEY: misc_feature
<223> OTHER INFORMATION: Description of Artificial Sequence: Primer

<400> SEQUENCE: 28
atagcacgga gcgagtggtg tc                                            22

<210> SEQ ID NO 29
<211> LENGTH: 18
<212> TYPE: DNA
<213> ORGANISM: Artificial sequence
<220> FEATURE:
<221> NAME/KEY: misc_feature
<223> OTHER INFORMATION: Description of Artificial Sequence: Primer

<400> SEQUENCE: 29
tcactctgaa gaattcac                                                 18

<210> SEQ ID NO 30
<211> LENGTH: 18
<212> TYPE: DNA
<213> ORGANISM: Artificial sequence
<220> FEATURE:
<221> NAME/KEY: misc_feature
<223> OTHER INFORMATION: Description of Artificial Sequence: Primer

<400> SEQUENCE: 30
tgagtgtgag aattccat                                                 18

<210> SEQ ID NO 31
<211> LENGTH: 18
<212> TYPE: DNA
<213> ORGANISM: Artificial sequence
<220> FEATURE:
<221> NAME/KEY: misc_feature
<223> OTHER INFORMATION: Description of Artificial Sequence: Primer -continued

```
<400> SEQUENCE: 31
gatcactctc cagttctt                                                 18

<210> SEQ ID NO 32
<211> LENGTH: 21
<212> TYPE: DNA
<213> ORGANISM: Artificial sequence
<220> FEATURE:
<221> NAME/KEY: misc_feature
<223> OTHER INFORMATION: Description of Artificial Sequence:  Primer

<400> SEQUENCE: 32
ggattttcgc agagatgcct g                                             21
```